(12) United States Patent
Sukuta

(10) Patent No.: US 12,085,505 B2
(45) Date of Patent: Sep. 10, 2024

(54) SPECTROSCOPIC METHOD AND APPARATUS FOR PREDICTION OF NON-ALCOHOLIC AND ALCOHOLIC BEVERAGES QUALITY PARAMETERS AND PROPERTIES

(71) Applicant: Brewmetrix LLC, Incline Village, NV (US)

(72) Inventor: Sydney Sukuta, Patterson, CA (US)

(73) Assignee: Spectrametrix, LLC, Incline Village, NV (US)

( * ) Notice: Subject to any disclaimer, the term of this patent is extended or adjusted under 35 U.S.C. 154(b) by 180 days.

(21) Appl. No.: 17/403,455

(22) Filed: Aug. 16, 2021

(65) Prior Publication Data

US 2022/0082497 A1 Mar. 17, 2022

Related U.S. Application Data

(63) Continuation-in-part of application No. 14/622,636, filed on Feb. 13, 2015, now Pat. No. 11,093,869.

(60) Provisional application No. 63/075,804, filed on Sep. 8, 2020, provisional application No. 62/092,080, filed on Dec. 15, 2014, provisional application No. 61/939,543, filed on Feb. 13, 2014.

(51) Int. Cl.
| | | |
|---|---|---|
| *G01N 21/3577* | (2014.01) | |
| *G01N 21/33* | (2006.01) | |
| *G01N 21/359* | (2014.01) | |
| *G01N 33/14* | (2006.01) | |

(52) U.S. Cl.
CPC ......... *G01N 21/3577* (2013.01); *G01N 21/33* (2013.01); *G01N 21/359* (2013.01); *G01N 33/146* (2013.01); *G01N 2201/0646* (2013.01)

(58) Field of Classification Search
None
See application file for complete search history.

(56) References Cited

U.S. PATENT DOCUMENTS

| | | | | |
|---|---|---|---|---|
| 5,262,961 A | * | 11/1993 | Farone | G01J 3/28 702/23 |
| 5,351,198 A | * | 9/1994 | Adachi | G01N 21/31 702/24 |
| 5,453,619 A | * | 9/1995 | Asselain | G01N 21/3577 250/339.04 |
| 7,194,369 B2 | * | 3/2007 | Lundstedt | G01N 35/00871 702/104 |

(Continued)

FOREIGN PATENT DOCUMENTS

DE 10217168 A1 * 1/2004 ............. G01N 21/31

OTHER PUBLICATIONS

DE10217168A1, translation (Year: 2004).*

*Primary Examiner* — Lina Cordero
(74) *Attorney, Agent, or Firm* — Ian F. Burns; ATIP Law

(57) ABSTRACT

Parameters of an alcoholic or non-alcoholic beverage can be determined through spectroscopic methods. In one example, the method includes obtaining a beverage sample and obtaining spectrographic data from the beverage. The spectroscopic data may be processed by a remote lab to determine a value range of the one or more beverage parameters, and a value of the one or more beverage parameters. The one or more beverage parameters may include one or more of beverage color, bitterness, Free Amino Nitrogen (FAN), yeast count and yeast viability.

17 Claims, 55 Drawing Sheets

(56) References Cited

U.S. PATENT DOCUMENTS

| | | | |
|---|---|---|---|
| 2002/0084415 A1* | 7/2002 | Kawano | G01N 21/03 250/339.09 |
| 2002/0106716 A1* | 8/2002 | Leboeuf | G01N 21/3577 702/19 |
| 2003/0025909 A1* | 2/2003 | Hallstadius | A23L 3/3409 53/167 |
| 2015/0227863 A1* | 8/2015 | Sukuta | G16C 20/70 705/7.11 |

* cited by examiner

| P1 CLASSES | CLASSIFIER MODEL RANGE (A.U.) | P2 CLASSES | CLASSIFIER MODEL RANGE (A.U.) |
|---|---|---|---|
| CLASS P1.1 | 1.95 TO 2.11 | CLASS P2.1 | 11.23 TO 11.76 |
| CLASS P1.2 | 2.12 TO 2.21 | CLASS P2.2 | 11.77 TO 12.24 |
| CLASS P1.3 | 2.22 TO 2.27 | CLASS P2.3 | 12.25 TO 12.35 |
| CLASS P1.4 | 2.28 TO 2.36 | CLASS P2.4 | 12.36 TO 13.11 |
| CLASS P1.5 | 2.37 TO 2.67 | CLASS P2.5 | 13.12 TO 13.66 |
| CLASS P1.6 | 2.68 TO 2.81 | CLASS P2.6 | 13.67 TO 13.88 |
| CLASS P1.7 | 2.82 TO 2.91 | CLASS P2.7 | 13.89 TO 14.26 |
| CLASS P1.8 | 2.92 TO 3.00 | CLASS P2.8 | 14.27 TO 15.46 |
| CLASS P1.9 | 3.01 TO 3.08 | CLASS P2.9 | 15.47 TO 16.46 |
| CLASS P1.10 | 3.09 TO 3.12 | CLASS P2.10 | 16.47 TO 17.29 |

KEY: P=PARAMETER

EACH PARAMETER OR MEASUREMENT RANGE IS A CLASS

FIG. 7

| P1 CLASSES | CALIBRATION MODEL RANGE (A.U.) | P2 CLASSES | CALIBRATION MODEL RANGE (A.U.) |
|---|---|---|---|
| CLASS P1.1 | 1.95 TO 2.11 | CLASS P2.1 | 11.23 TO 11.76 |
| CLASS P1.2 | 2.12 TO 2.21 | CLASS P2.2 | 11.77 TO 12.24 |
| CLASS P1.3 | 2.22 TO 2.27 | CLASS P2.3 | 12.25 TO 12.35 |
| CLASS P1.4 | 2.28 TO 2.36 | CLASS P2.4 | 12.36 TO 13.11 |
| CLASS P1.5 | 2.37 TO 2.67 | CLASS P2.5 | 13.12 TO 13.66 |
| CLASS P1.6 | 2.68 TO 2.81 | CLASS P2.6 | 13.67 TO 13.88 |
| CLASS P1.7 | 2.82 TO 2.91 | CLASS P2.7 | 13.89 TO 14.26 |
| CLASS P1.8 | 2.92 TO 3.00 | CLASS P2.8 | 14.27 TO 15.46 |
| CLASS P1.9 | 3.01 TO 3.08 | CLASS P2.9 | 15.47 TO 16.46 |
| CLASS P1.10 | 3.09 TO 3.12 | CLASS P2.10 | 16.47 TO 17.29 |

FIG. 9

SUMMARY OF ANALYTICAL REGIONS RMSEP

| ANALYTICAL REGION | PRE-OUTLIER RMSEP | POST-OUTLIER RMSEP |
|---|---|---|
| 1 | .13 | .06 |
| 2 | .09 | .03 |
| 3 | .05 | .05 |
| 4 | .16 | .08 |
| 5 | .06 | .06 |
| 6 | .01 | .01 |
| 7 | .17 | .04 |

FIG. 21

SUMMARY ANALYTICAL CLASSES CUT-OFF POINTS

| ANALYTICAL REGION/CLASS | MEASURED MIN (%) | POINTS MAX (%) | MERGED MIN (%) | POINTS MAX (%) |
|---|---|---|---|---|
| 1 | 11.23 | 12.12 | 11.23 | 12.15 |
| 2 | 12.18 | 12.44 | 12.16 | 12.63 |
| 3 | 12.83 | 13.25 | 12.64 | 13.39 |
| 4 | 13.52 | 14.02 | 13.4 | 14.05 |
| 5 | 14.08 | 15.56 | 14.06 | 15.41 |
| 6 | 15.26 | 16.59 | 15.42 | 16.59 |
| 7 | 16.6 | 17.29 | 16.6 | 17.29 |

FIG. 23

EXAMPLE OF MEMBERSHIP DETERMINATION OUTPUT

| SAMPLE ID | MS SCORE CLASS 1 | CLASS 1 MEMBER | MS SCORE CLASS 2 | CLASS 2 MEMBER 2 |
|---|---|---|---|---|
| BBCP5 | 0.894976 | YES | 0.105024 | NO |
| BBCP6 | 0.85902 | YES | 0.14098 | NO |
| BBKO1 | 1.12553 | YES | -0.12553 | NO |
| BBKO2 | 1.15359 | YES | -0.15359 | NO |
| BBKO3 | 0.9009 | YES | 0.0991 | NO |
| BBKO4 | 0.879891 | YES | 0.120109 | NO |

FIG. 24

B. ONE-TIME PRODUCT PRE-CONFIGURATION WIZARD
BELOW ARE THE INDUSTRIES WE CURRENTLY SERVICE.
SELECT ONE

| | |
|---|---|
| WINERY | SELECT |
| BEER BREWING | SELECT |
| DAIRY | SELECT |
| WINERY | SELECT |
| ETC. | |

IF YOUR INDUSTRY IS NOT LISTED CONTACT US
xxxx@yyyy.com

FIG. 26

B. WELCOME TO THE ONE-TIME
PRODUCT PRE-CONFIGURATION WIZARD.

ONCE CONFIGURED YOU WILL BE ABLE TO MEASURE AT ONCE AND FOR EACH OF THE FOLLOWING BREWING STAGES

| A. WORT | B. PRE-FILTRATION (PF), | C. END-OF-FILTRATION (EF) |
|---|---|---|
| D. BRIGHT-TANK (BT): | E. BOTTLED BEER (BB): | |

THE FOLLOWING PARAMETERS
1. SUGAR ORIGINAL EXTRACT (%) (PEO).
2. SUGAR APPARENT EXTRACT (%) PEA
3. ALCOHOL (%) (EXCEPT FOR WORT),
4. BITTERNESS (IBU),
5. COLOR, (EBC)
6. pH

YOU MUST HAVE EACH PRODUCT'S PARAMETERS FIRST MEASURED USING A REFERENCE METHOD OF YOUR CHOICE BEFORE PROCEEDING TO THE NEXT STEP.

FIG. 27

B. THE ONE-TIME PRE-CONFIGURATION WIZARD.

CHECK THE PROGRESS STAGE(S) YOU WOULD LIKE TO CONFIGURE

| PROCESS STAGE | CHECK BOX |
|---|---|
| A. WORT | |
| B. PRE-FILTRATION (PF), | |
| C. END-OF-FILTRATION (EF) | |
| D. BRIGHT TANK (BT) | |
| E. BOTTLED BEER (BB): | |

FIG. 28

| ENTER BREW NAME [E.G. MA] FINAL OUTPUT = LFMA | RANGE OF EXPECTED RESULTS (SEE RANGE TABLE FOR WORT ON THE NEXT PAGE) |
|---|---|
| 1. ORIGINAL EXTRACT [%] (PEO) | ALLOW UP TO TWO CONSECUTIVE RANGES TO BE ENTERED IN THIS COLUMN AND OUR SYSTEM WILL CHOOSE THE BEST ANALYTICAL REGION BETWEEN THE TWO. ONE ENTRY IS MANDATORY AND THE SECOND ONE IS OPTIONAL. |
| 2. APPARENT EXTRACT (%) (PEA) | |
| 3. ALCOHOL (%) *(IF WORT THIS OPTION MUST BE GRAYED OUT) | |
| 5. COLOR (EBC) | |
| 6. BITTERNESS (IBU) | |
| 7. pH (ONLY AVAILABLE FOR WORT) | |

FIG. 29

B. DESIGNATED WORT SUGAR EXTRACT RANGES
SUGAR EXTRACT (PEO/PEA)(%)

| RANGE/CLASS | MIN | MAX |
|---|---|---|
| 1 | 10.95 | 11.67 |
| 2 | 12.06 | 12.38 |
| 3 | 12.4 | 12.64 |
| 4 | 12.64 | 12.9 |
| 5 | 12.91 | 13.13 |
| 6 | 13.14 | 13.39 |
| 7 | 13.39 | 13.7 |
| 8 | 14.44 | 14.64 |
| 9 | 14.65 | 14.86 |
| 10 | 14.86 | 15.16 |
| 11 | 15.32 | 15.76 |
| 12 | 16.19 | 16.88 |
| 13 | 16.76 | 17.09 |
| 14 | 17.34 | 17.84 |
| 15 | 17.91 | 18.72 |

FIG. 30

| PFCP. 2013_06_16 | OUTPUT RANGE VALIDATION | RECOMMEND. OUTPUT RANGE | PREDICT ALL (OVERRIDES ALL BELOW) |
|---|---|---|---|
| PEO | PASS | GRAY-OUT | PREDICT |
| % ALCOHOL | PASS | GRAY-OUT | PREDICT |
| BITTERNESS | FAIL | 30 TO 40 IBU | DO NOT PREDICT |
| ETC... | | | |

FIG. 31

| SUBSCRIBER COMPANY: COMPANY XYZ<br>BREW STAGE AND DATE: PFCP. MM/DD/YYYY<br>TECHNICIAN: RYAN<br>TODAY'S DATE MM/DD/YYYY | OUTPUT RANGE | RESULTS |
|---|---|---|
| PEO (1-CREDIT) | 10 TO 15% | 12% |
| % ALCOHOL (1-CREDIT) | 5 TO 10% | 8% |
| BITTERNESS (1-CREDIT) | 30 TO 40 (IBU) | 35 (IBU) |
| | | CREDITS USED THIS SESSION = 3<br>TOTAL CREDITS USED: 233<br>CREDITS LEFT = 267 |

WOULD YOU LIKE TO DO ANOTHER TEST ANOTHER BEER PRODUCT CHECK-UP?  YES  NO

WOULD YOU LIKE TO CHECK-UP RESULTS SENT TO THE SUBSCRIBER E-MAIL ACCOUNT OF FILE?  YES  NO

FIG. 32

YEAST VIASBILITY PREDICTIONS

| % VIABILITY RESULTS | | TEST SET (ts) | | |
|---|---|---|---|---|
| | | OBSERVED (%) | PREDICTED (%) | % ERROR |
| 11  WYEAST 1 | ts | 74 | 78.5929 | 4.59294 |
| 15  WYEAST 1 | ts | 74 | 75.9067 | 1.90667 |
| 21  WYEAST 2 | ts | 97 | 96.3194 | 0.680595 |
| 25  WYEAST 2 | ts | 97 | 93.5632 | 3.43678 |
| 31  WYEAST 3 | ts | 65 | 58.6627 | 6.33735 |
| 35  WYEAST 4 | ts | 65 | 64.4184 | 0.581635 |
| | | | | 17.53597 |
| | | | | AVG=2.92% |

FIG. 54

YEAST COUNTS PREDICTIONS

| | OBS ID (PRIMARY) | OBSERVED COUNTS | PREDICTED COUNTS |
|---|---|---|---|
| PREDICTION SAMPLES | PRED10561 | | 9.82E+08 |
| | PRED10562 | | 9.80E+08 |
| | PRED10563 | | 9.81E+08 |
| | PRED10564 | | 9.80E+08 |
| | PRED10565 | | 9.80E+08 |
| | PRED10566 | | 9.80E+08 |
| | PRED10567 | | 9.78E+08 |
| | PRED10568 | | 9.81E+08 |
| | PRED10569 | | 9.78E+08 |
| | PRED105610 | | 9.77E+08 |
| REFERENCE SAMPLES | REF 127511 | 6.50E+08 | 6.45E+08 |
| | REF 127512 | 6.50E+08 | 6.44E+08 |
| | REF 127513 | 6.50E+08 | 6.50E+08 |
| | REF 127514 | 6.50E+08 | 6.51E+08 |
| | REF 127515 | 6.50E+08 | 6.52E+08 |
| | REF 127516 | 6.50E+08 | 6.52E+08 |
| | REF 127517 | 6.50E+08 | 6.53E+08 |
| | REF 127518 | 6.50E+08 | 6.52E+08 |
| | REF 127519 | 6.50E+08 | 6.49E+08 |
| | REF 127520 | 6.50E+08 | 6.52E+08 |
| | REF 127521 | 1.17E+09 | 1.17E+09 |
| | REF 127522 | 1.17E+09 | 1.17E+09 |
| | REF 127523 | 1.17E+09 | 1.17E+09 |
| | REF 127524 | 1.17E+09 | 1.17E+09 |
| | REF 127525 | 1.17E+09 | 1.17E+09 |
| | REF 127526 | 1.17E+09 | 1.17E+09 |
| | REF 127527 | 1.17E+09 | 1.17E+09 |
| | REF 127528 | 1.17E+09 | 1.17E+09 |
| | REF 127529 | 1.17E+09 | 1.17E+09 |

FIG. 56

SPECTROSCOPIC METHOD AND APPARATUS FOR PREDICTION OF NON-ALCOHOLIC AND ALCOHOLIC BEVERAGES QUALITY PARAMETERS AND PROPERTIES

CROSS REFERENCE TO RELATED APPLICATIONS

This application is a continuation-in-part of U.S. patent application Ser. No. 14/622,636, filed 13 Feb. 2015, which claims priority to U.S. provisional patent application Ser. No. 61/939,543, filed 13 Feb. 2014 and 62/092,080 filed 15 Dec. 2014. This application also claims priority to U.S. Provisional Patent Application No. 63/075,804 filed Sep. 2020. The contents of each of these applications is herein incorporated by reference.

FIELD OF THE INVENTION

The present invention relates to analytical systems and in particular to systems and methods for performing analysis of non-alcoholic and alcoholic beverages, particularly alcoholic beverages to predict their quality parameters, and predicting the presence of alcohol in "non-alcoholic" beverages where it may be intentionally concealed or undeclared.

BACKGROUND

There are many uses for analyzing one or more properties of material. Such analytical systems are commonly considered useful for the agricultural, medical, food and beverage, mining, chemical, and finished hard goods industries, although the analytical systems are not limited to these industries, nor are they limited to industrial use. As one non-limiting example of industrial use, pharmaceutical companies may analyze the concentration of various components of a drug during multiple stages of its production to ensure it meets applicable standards.

Most traditional laboratory tests used to analyze properties of materials or samples require 1) a high degree of training and specialization in analytical lab methods, 2) the use of a physical plant, and 3) a significant commitment of funding and time. Non-experts who may want to perform their own tests may then be challenged in cases where they lack the necessary training, funding, and/or locational mobility. Furthermore, users often require multiple machines to test multiple properties of interest of a material or sample in question.

A handful of analytical systems have been proposed—for example, in U.S. Pat. No. 6,560,546 (2003) to Shenk and Westerhaus, U.S. Pat. No. 7,630,848 (2009) to Loosme, U.S. Pat. No. 7,194,369 (2007), and U.S. Pat. No. 8,010,309 (2011) all to Lundstdt et al.

While conventional analytical systems and methods as well as the prior art are generally thought to provide acceptable performance, they also include shortcomings. The prior art generally states that in the data processor, an appropriate calibration model is selected to analyze the data and results are made available thereafter. The prior art neglects to explain, however, the methods by which the appropriate models are selected. A further shortcoming is that the prior art systems are not well configured for data that exhibits non-linear responses and thus they are quite limited. Consequently, without methods to handle nonlinear responses, there are likely to be unacceptable prediction errors and/or samples that do not exhibit a linear response could be declared as outliers. This therefore limits the scope of the prior art to include only sample responses that are perfectly linear.

The prior art also limits user access to the results of the data at the end of one analytical system. In addition, the results of the analysis from existing analytical systems remains inaccessible to non-experts since the systems do not include a user interface that displays results through a modality that non-experts can more easily comprehend.

When it comes to analyzing non-alcoholic beverage samples to determine the presence of alcohol, samples of the beverage are required to be sent to a lab for analysis. There can be issues with the handling and time taken to analyze and provide results. For example, in a highway patrol interception of a subject driving and drinking or employee drinking on the job there are currently no means to test and verify the presence/absence of alcohol without the aid of a certified lab. Also, some non-alcoholic drinks with yeast may ferment to produce alcohol beyond the legally allowed limit. The culprits, and unsuspecting consumers, could then consume a "non-alcoholic" beverage and get intoxicated unabated. Thus, it would be preferable if "non-alcoholic" beverages could be tested and results generated and provided in near real-time and at the point of interception.

What is required is an improved system and method for performing analysis.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to predict quality parameters and properties in a non-alcoholic and/or alcoholic beverage;

the ability to predict beverage quality parameters with minimal equipment;

the ability to predict quality parameters and properties at any location in or outside a laboratory;

minimize prediction errors, particularly when the response variable exhibits are non-linear;

provide flexibility for the user to retrieve results from any location from which the internet can be accessed;

provide results in a user friendly manner that non-experts can easily understand;

provide users with the option to access results at various stages of the analytical process; and the ability to allow users the flexibility to conduct examinations and to analyze results from a location remote from the substance in question.

These and other advantages may be realized by reference to the remaining portions of the specification, claims, and abstract.

Brief Description of One Embodiment of the Present Invention

In one aspect, the invention provides a method for determining one or more beverage parameters of a beverage. The method may comprise obtaining a beverage sample, obtaining spectrographic data from the beverage, determining by a data processor and from the spectrographic data, a value range of the one or more beverage parameters, and determining by a data processor and from the spectrographic data, a value of the one or more beverage parameters. The one or more beverage parameters may include one or more of beverage color, bitterness, Free Amino Nitrogen (FAN), yeast count and yeast viability.

In one aspect, the invention provides a system for analyzing a beverage. The system may include spectroscopic apparatus and a data processor. The spectroscopic apparatus may be configured to receive a beverage sample and dispose the beverage sample in a light beam to obtain spectrographic data of the beverage sample. The data processor may be programmed to receive the spectrographic data from the spectroscopic apparatus, determine a value range of at least one beverage parameter of the sample, and determine the value of the at least one beverage parameter from the spectrographic data.

In one aspect, the invention provides a sensor unit. The sensor unit comprises a sample holder for receiving a beverage sample, a light source configured to direct light into the beverage sample, and a spectrometer for receiving light altered by the beverage sample and processing the received light to obtain spectrographic data of the beverage sample.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 7. is a sample library of parameter classifier models;

FIG. 9. is a sample library of quantifications that associates classes with ranges;

FIG. 21 is a summary table of the RMSEP values for the analytical regions prior to and after removing outliers;

FIG. 23 is a table that shows the cut off points for the analytical classes;

FIG. 24 is a table that shows an example of a membership determination output;

FIG. 26 shows an industry selection interface;

FIG. 27 shows an introductory interface for a pre-configuration wizard;

FIG. 28 shows a parameter selection interface for the pre-configuration wizard;

FIG. 29 shows a range entry interface for the selected parameters;

FIG. 30 shows example range table for a parameter;

FIG. 31 shows a validation interface;

FIG. 32 shows a results interface;

FIG. 54 shows a yeast viability table for a beverage;

FIG. 56 shows a yeast count table for a beverage.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized, and structural changes may be made without departing from the scope of the present invention.

Figure 1:
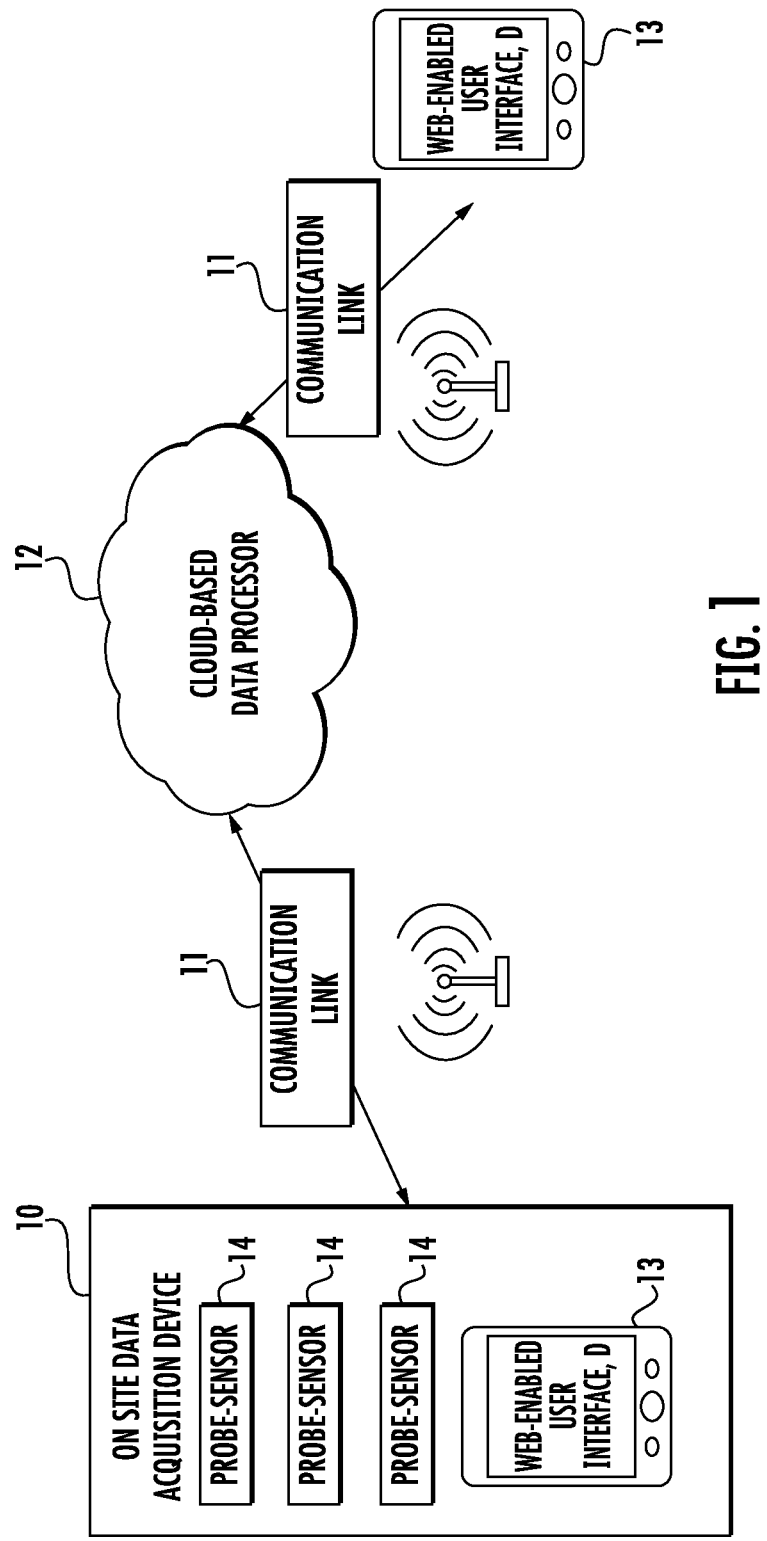
FIG. 1. is a block diagram illustrating the system architecture.

It has been found by the present inventors that spectrographic systems can be used to determine or predict Color of Bitterness of, and Free Amino Nitrogen (FAN) in alcoholic beverages, and yeast counts and yeast viability in fermentation/fermentation products, and the presence of alcohol in "non-alcoholic" beverages. The alcoholic beverage parameters/properties and fermentation yeast have characteristic wavelength signatures that enable us to detect and characterize them by spectrographic techniques. An embodiment of the invention is described with reference to the figures using reference designations as shown in the figures. FIG. 1 shows the system architecture which comprises at least one on site data acquisition device 10 comprising at least one probe sensor 14 to interrogate the product or substance in question, a cloud-based data processor (data processor) 12 having at least one computer processor to analyze the data and compute results, a web enabled user interface (user interface) 13 to display results on a user computer device in a format that is accessible to non-experts, and in this embodiment two bidirectional communication links 11, one that sends data between the cloud-based data processor 12 and the on site data acquisition device 10 and the other that sends data between the cloud-based data processor 12 and the web-enabled user interface 13.

Figure 2:
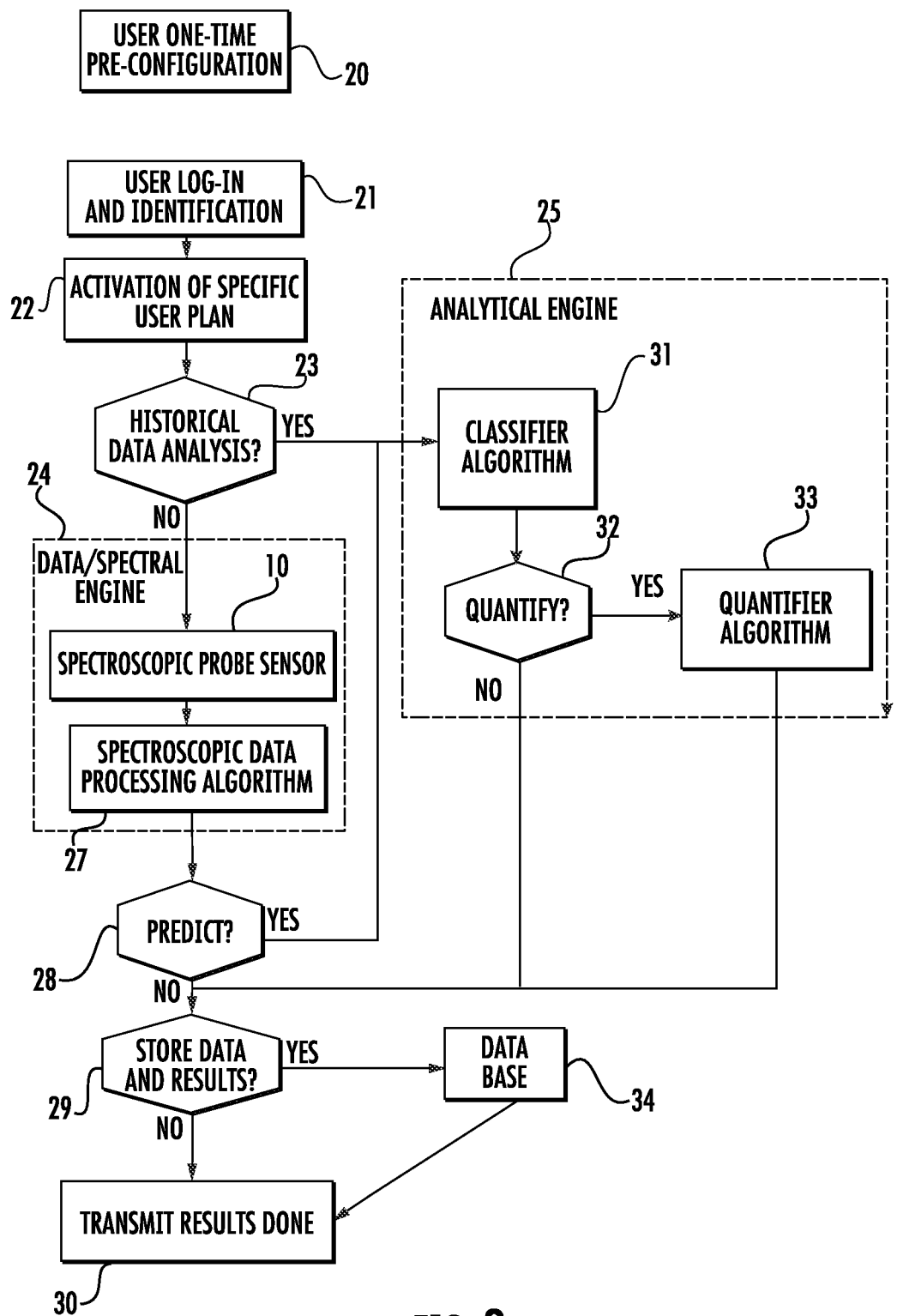
FIG. 2. is a flow chart to establish model feasibility, development, and use.
Figure 3:
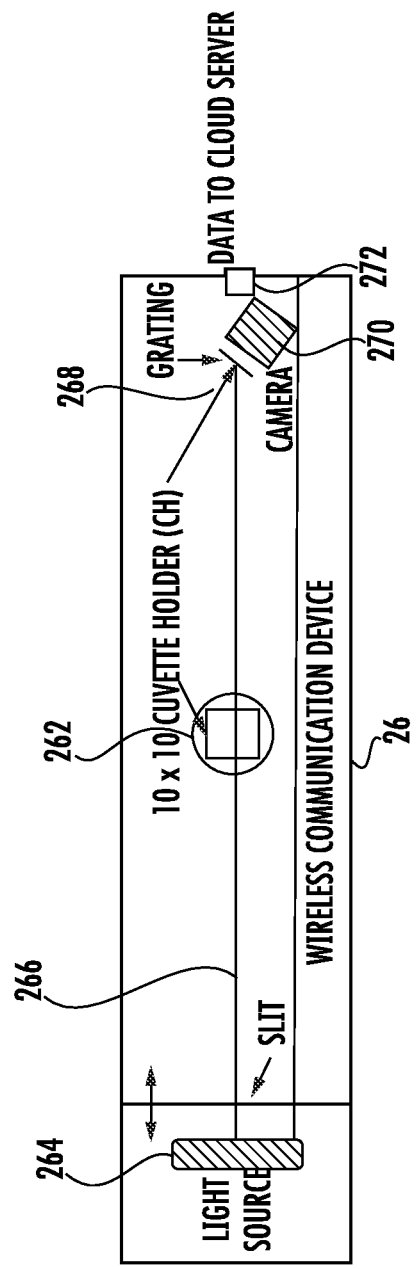
FIG. 3. is an upper perspective view of an example probe-sensor unit.

In this embodiment, the data acquisition device 10 is the apparatus further described in FIG. 3 that collects the data from the substance in question and transfers it to the cloud-based data processor 12 via a communication link 11. In the data processor 12, the data is analyzed as further described in FIGS. 2, 4, 5, and 8. The data is then transferred to a web-based user interface which may be installed on any web enabled device including but not limited to a data acquisition device 10 computer, cellular phone, or tablet. The user interface 13 displays the information in a format that makes the results easy to understand for non-experts.

Bidirectional communication links 11 are responsible for connecting the components 10, 12, 13 in FIG. 1 and can include a plurality of telecommunication modes. Buffering capabilities are stored in the user interface, cloud-based data processor, and data acquisition device to ensure signal integrity and retention in the event that the communication network temporarily fails to transmit signals in real-time.

Figure 10:
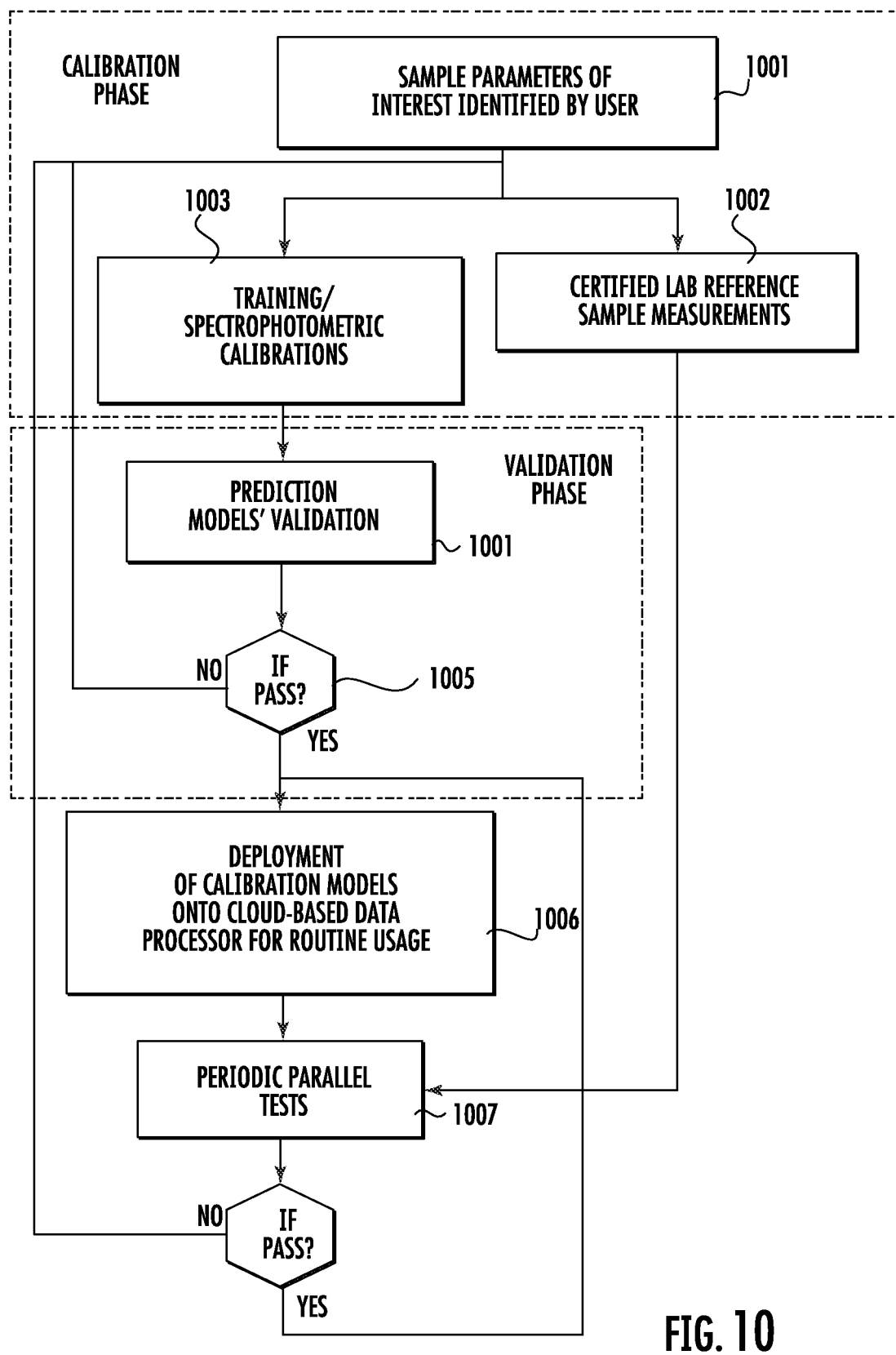
FIG. 10 is a flow chart describing how the sample parameters of interest are determined.

FIG. 10 is a flowchart which demonstrates how the initial parameters of the virus in question are analyzed and applied to the calibration models stored on the cloud-based data processor. For example, the user may wish to configure the system to examine a number of different biological pathogens, such as viruses, each pathogen having its own characteristic wavelength signature or spectrograph. Once the user pre-selects the pathogen of interest 1001, the samples are analyzed in two ways. One is by using a certified lab reference 1002, the other by probing samples from the certified lab in the form of a training set using spectroscopic means 1003. A correlation between the training data set and the certified lab results is identified. A mathematical relationship between the results from the certified lab and the identified spectral points is then developed for the training set. From here, calibration prediction models are used to predict declared parameters from samples other than the training set 1004. If the prediction errors are beyond an acceptable limit (determination 1005), the prediction model is deemed unacceptable and the process begins again from the training/spectrophotometric calibrations and certified lab reference sample measurements. If the prediction model is deemed acceptable, the model is deployed onto the cloud-based data processor 1006. Tests analyzing specified parameters of interest between a certified lab and the prediction model used in the cloud-based data processor are parallel tested periodically 1007 to ensure there are no drifts. In cases where a periodic test fails, the associated prediction model is sent back to the Training/Spectrophotometric Calibrations step of the process.

FIG. 2 is a flowchart which demonstrates the feasibility of the invention. The process shows the way the data is obtained, computed, stored, and displayed, as well as how the user interacts with the system. During the initial use as shown in block 20, the system undergoes a one-time pre-configuration completed by the user using the web-enabled user interface 11.

During all subsequent uses, the system is initiated through block 21, a user log-in and identification. One object of block 21 is to retrieve historical data and present analytical options specific to the user. Thus the successful application of block 21 automates the activation of block 22 which retrieves the specific user plan. Then, in block 23, the user is given an option to either select data previously collected, or to collect new data to be analyzed.

Figure 4:
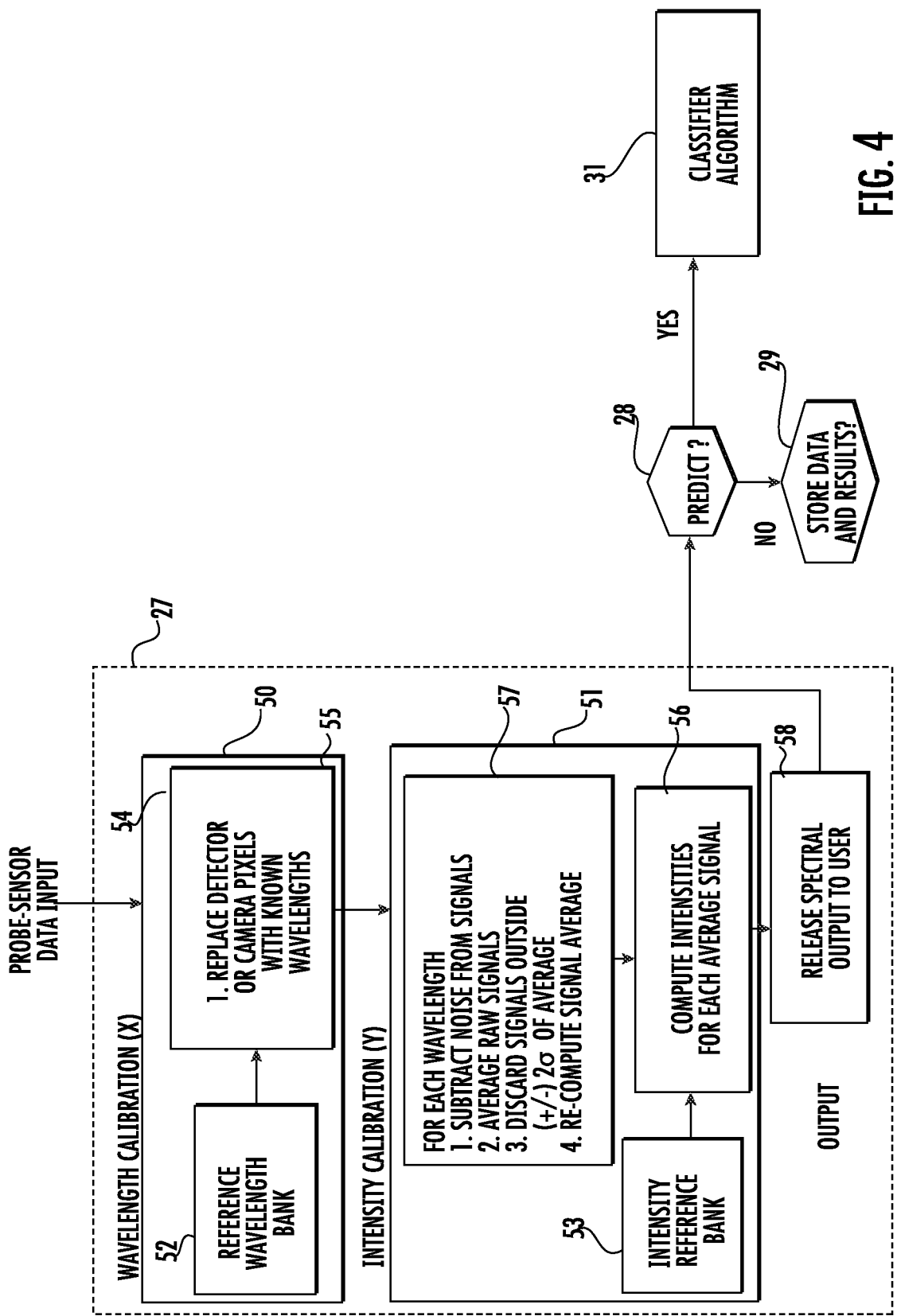
FIG. 4. is a flow chart demonstrating development and use of a Data/Spectral Engine.

In cases when historical data analysis is not selected, the spectroscopic probe sensor 10 is employed to collect data from the substance in question, such as a biological sample, and transfers that data using a communication link 11 to the cloud-based data processor 12 where the data is analyzed using a spectroscopic data processing algorithm 27 as shown in the data/spectral engine 24 and further described in FIG. 4. Once analyzed in block 27, control goes back to block 28. Depending on the user preferences selected at the time of system configuration, results are either displayed on the user interface 13 or the data is sent to the classifier algorithm 31 in the analytical engine 25 to undergo further analysis.

The analytical engine 25 includes two algorithms: the classifier algorithm 31 and the quantifier algorithm 33. The object of the classifier algorithm 31 is to approximate the ranges of the sample properties of interest i.e. parameters characterizing the sample. After data passes through block 31, it either transfers to the quantifier algorithm 33 to undergo further analysis, or the results are displayed, pending user preferences at the time of system configuration. The classifier algorithm 31 is further detailed in FIG. 5. In cases where the sample data transfers to the quantifier algorithm 33, it undergoes further interrogation to precisely predict values for the sample properties of interest i.e. parameters characterizing the sample. The quantifier algorithm is further detailed in FIG. 8. Once the data in block 33 has been analyzed, it transfers to block 29 where the results may be stored in a database prior to displaying on the web-enabled user interface 13. Alternatively, results may directly transmit to the user interface 13 or any other web-enabled device of choice. Once results are transmitted in block 30, the process has finished.

Figure 11:
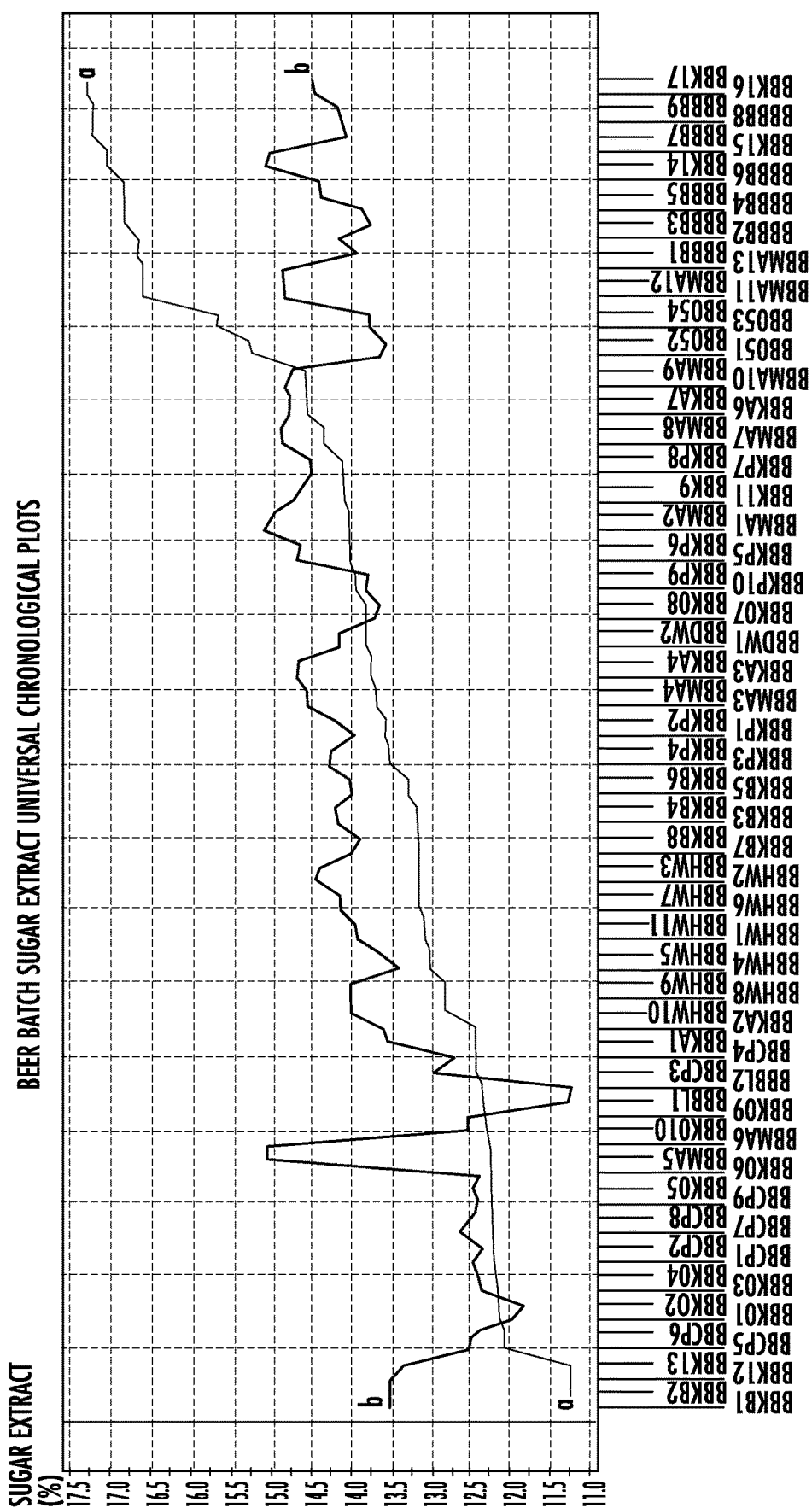
FIG. 11 is a graph depicting both standard reference model results plotted against Universal Calibration Model results which were taken from actual samples of sugar content measured from a beer batch.

The example in FIG. 11 shows how this analytical system improves accuracy of results when compared to conventional methods. This example shows the results from a test of original sugar percent of a beer batch in production. The example is included here to demonstrate the suitability of the presently described methods for processing spectroscopic data in sample types that have non-linear responses. The methods can be similarly applied to both non-alcoholic and alcoholic beverages to determine concentration amounts, yeast counts and viability, and presence/absence of alcohol in "non-alcoholic" beverages. The data in this figure show the results of a Partial Least Squares (PLS) universal calibration model which is referred to as the "Chronological Plot." The horizontal axis represents the different samples analyzed while the vertical axis represents the measurements of the samples' sugar extract. Line "A" represents the results measured from using standard reference methods.

Line "B" represents the output of the universal calibration model (UCM) developed using the reference method results and the spectral data for each sample. Ideally, Line B would track and overlap Line A very closely. However, because Line B is not similar to Line A, it is apparent that applying only the data results from the UCM to a sample parameter of interest, as per the prior art, does not produce the greatest accuracy. This figure demonstrates that the examples from prior art are limited to linear data.

FIG. 3 is a block diagram of a basic probe sensor data acquisition device 10, which may be used to collect sample data from a product or substance in question. This device operates by shooting light 266 from a light source 264 onto the substance in question. The light beam is then incident upon a grating 268 and finally a camera 270, thereby collecting pixels and signals to obtain a spectrographic sample. The light source 264 may produce light at any wavelength or set of wavelengths targeted at the particular substance or sample in question. For example, the light source may produce light in the visible, UV, near infra-red or infra-red regions. The light source 264 may include multiple sources that produce light in different wavelength bands.

A data processor and communications module 272 may provide some initial processing of the sample data and then communicate the spectrographic data to other components for additional processing. In one embodiment, the sample may be a vial or similar receptacle that is able to receive a biological sample of a subject. For example, the subject may spit or otherwise provide saliva into the vial. Other biological samples such as blood, urine, sweat, mucus etc. may be provided. The vial is placed in the cuvette holder 262 of the apparatus which supports the vial so that the vial interrupts the light beam. Other types of samples and sample collection devices will be apparent to the person skilled in the art. The probe sensor used in this analytical system transfers the data collected to a web-based server, via the communications module 272, through any type of wireless connection device, including but not limited to Wi-Fi, Bluetooth, and cellular radio.

In FIG. 4, the sample data transmitted from the data acquisition device 10 is transferred into the data/spectral engine 27 where the signals received are converted to a suitable data format. The data/spectral engine 27 is located in the data processor instead of the probe sensor. In block 50, a wavelength (x-axis) is assigned based on the average of the pixel readings and is calibrated using a reference wavelength bank 52. Then in block 51, the appropriate intensities for the sample reading are assigned. To initiate this process in block 57, the system subtracts noise from each wavelength signal. The raw signals are then averaged. After this step, any signals that fall within +/- two standard deviations outside of the mean are discarded and the remaining signals are then averaged again. At this stage, the final average for each signal is computed using the intensity reference bank 53 to assign the accurate intensity for the signal. The data is then released to the user through block 58. In block 28, the data either transfers to the classifier algorithm 31 to undergo further analysis, or it displays the results with the option to store them in block 29, depending on the user specifications.

Figure 5:
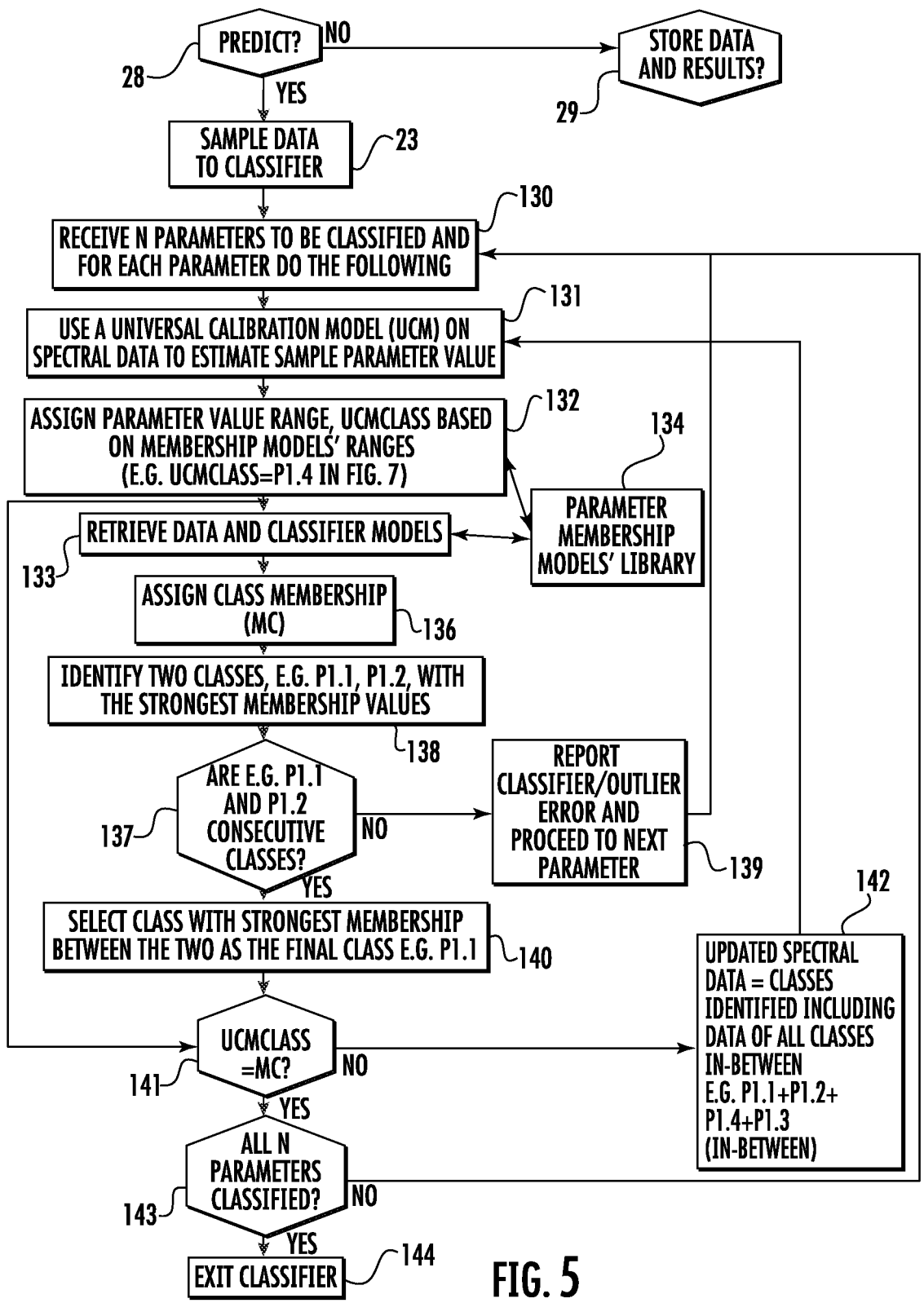
FIG. 5. is a flow chart describing the development and use of a Classifier Algorithm.
Figure 6:
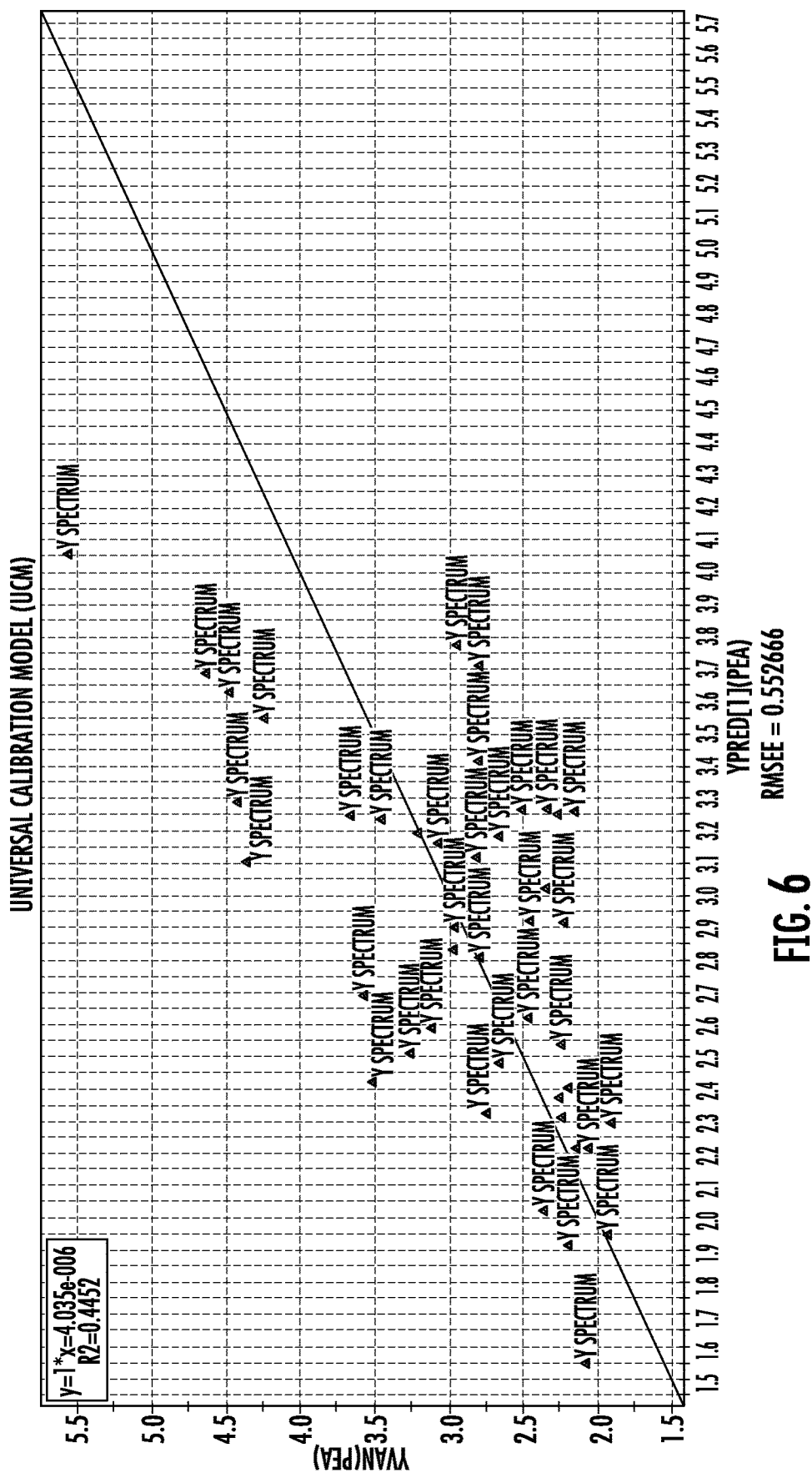
FIG. 6. is a prediction versus observed graph showing results of nonlinear data derived from samples of beer.

FIG. 5 demonstrates how samples that enter the classifier algorithm 31 are computed and analyzed. The classifier algorithm is responsible for determining results of the highest degree of accuracy possible, particularly when examining nonlinear data. In block 23, the sample data are transferred into the classifier and then assigned a predetermined number of parameters. Using the above example, if the substance in question is beer, the parameters assigned may include but are not limited to pH, sugar, or alcohol content. If the substance in question is a biological sample, the parameters assigned may be one or more virus types. Once parameters have been assigned, the data proceeds to block 131 where it is interrogated by a universal calibration model (UCM), crude classifier to compute a crude estimate for the value of each sample parameter. As an example, FIG. 6 shows the results from a UCM of a sample of beer plotted on a graph. Once the UCM 131 is finished, block 132 assigns a range of membership models to the sample data. The range is based on predetermined membership models ranges. FIG. 7 highlights one example of a predetermined membership model reference library. In FIG. 7, a P refers to each parameter or measurement range which is a class.

The sample parameter value determined using the UCM, block 131, and its assigned parameter value range are transferred to and stored in block 141 as the sample data continues to block 133 to be analyzed using the Parameter Membership Classifier Model (PMM). In block 133, the sample data is retrieved along with the parameter membership models library. Using the Parameter Membership Models' Library 134, the data is assigned a class membership in block 136. To achieve this, the system first splits the parameter classes in half between a Class Range A and Class Range B. Then the membership algorithm (PMM) is run to determine which half the sample parameter belongs to. If the PMM identifies the Class Range A as the membership of the parameter, then the parameter classes in Class Range A are split in half again into Class Range A1 and Class Range A2. Again, the membership algorithm is run, and this pattern continues until there are no more class memberships to split in half.

In block 140, the system selects the class with the strongest membership from blocks 138 and 137 and proceeds with this class as the final. The final class is transferred to Block 141 where it is compared against the results from the universal calibration model, which had been stored in block 141 earlier. If the two classes (the universal class and the membership class) are equal, the system recognizes that the desired level of accuracy has been reached and proceeds to block 143. If the two classes are not equal, the data is directed back to the crude classifier 131 to be computed again.

However, before the data reaches block 131, it must pass through block 142 where the system discards all of the data that exists outside of the range identified between the crude classifier 131 and the membership classifier 136. For example, consider the sample of beer in FIG. 6 and imagine the crude classifier 131 estimates its value on the x-axis as 4.0 while the membership classifier 136 estimates it at 4.4. In this case, the system would dispose of all the data points less than 4.0 and greater than 4.4 before proceeding with the cycle again starting with block 131. This cycle is repeated in the classifier until the point that the data from the UCM 131 and the Membership classifier 136 matches in block 141. Once the data matches, the system checks to see if all of the sample parameters have been classified. If so, the data exits the classifier 144. If not, the system begins again at block 130 where it identifies the parameter(s) that remains to be classified.

There are several other parameter classification algorithms that can be applied during the classifying stage. The PMM classification scheme is suitable for multiple classes, but in some examples and practical application, it may be preferable to work with two samples at a time. As the algorithm narrows down the class ranges, it is able to improve accuracy at capturing the results from nonlinear data. This is in comparison to the prior art which typically only applies a UCM calculation (crude estimate) to arrive at the final result.

Figure 8:
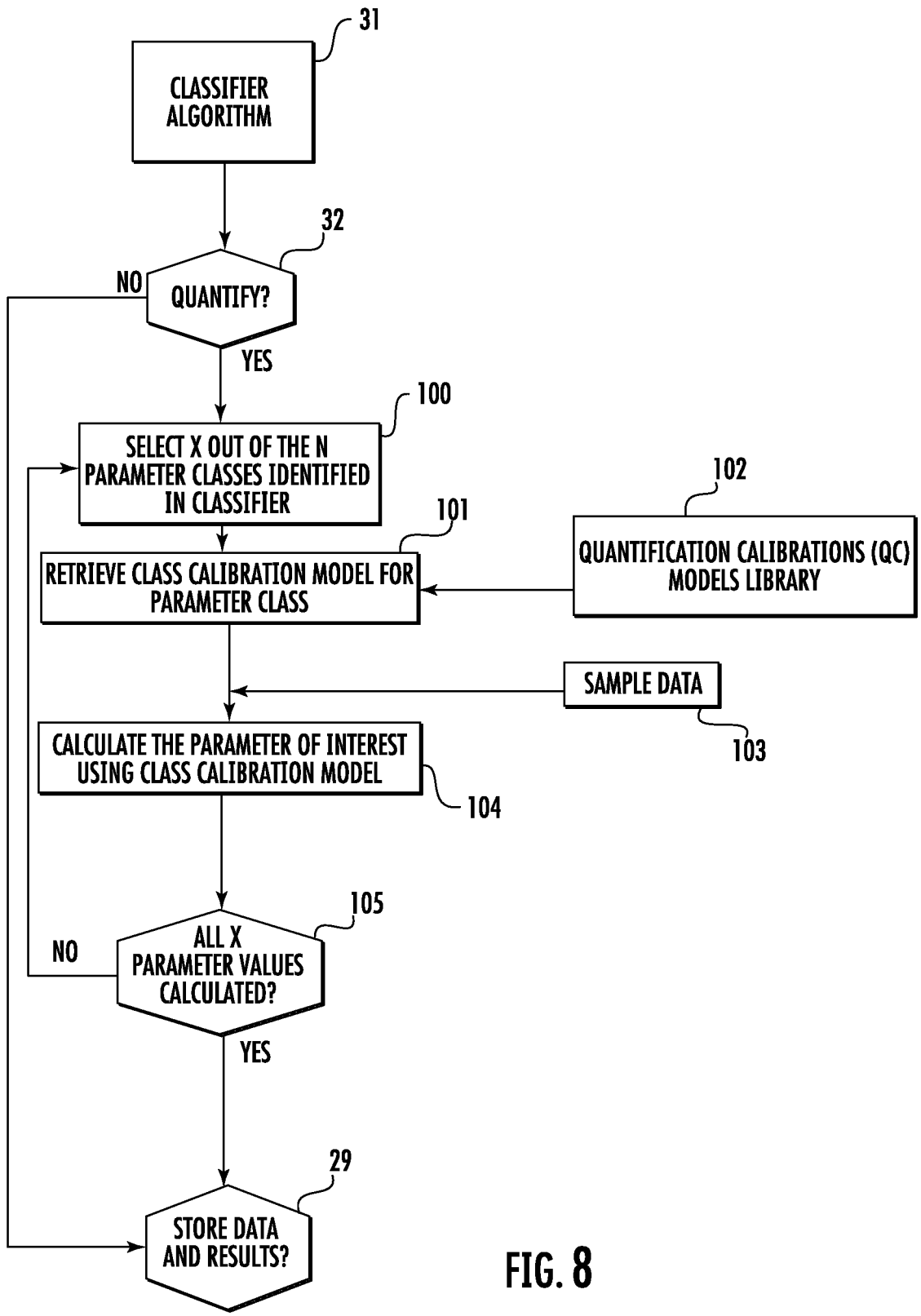
FIG. 8. is a flow chart describing the development and use of a Quantifier Algorithm.

After the classifier has determined the classes for all parameters of the sample in question, the system initiates the quantifier algorithm 33, shown in FIG. 8. The objective of the quantifier 33 is to calculate the precise value of each parameter in question based on the narrow range provided in the classifier.

In cases where the user programs the system to display results after the classifier, block 32 will automatically send the data to block 29 where results are either stored and displayed or immediately displayed depending on the user's pre-programmed preferences. In cases where the user chooses to run the sample through the quantifier, block 32 automates the initiation of block 100 where the system identifies all parameters that were analyzed in the classifier 31 and automates the quantifier 33 to quantify a final value for each of the parameters in question. Like the classifier in FIG. 5, the quantifier deals with each parameter sequentially. In block 101, the quantifier retrieves the appropriate equations for the parameter class by referencing the Quantifications Calibration Models Library 102. The system then receives the sample data 103, and calculates the parameter of interest value using the appropriate class calibration model in block 104. FIG. 9 shows an example of the Quantifications Library that associates classes with ranges. In FIG. 9, each Prefers to a parameter or measurement range which is a class. Once the value is calculated, the system checks in block 105 if all of the parameters from the classifier 31 have been quantified. If not, the system initiates again in block 100 to select a remaining parameter, and will run through this cycle (block 100-105) until all parameters are quantified. Once quantified, the data results proceed to block 29 where the system computes whether to store the data or immediately display results depending on the user preference.

Figure 12:
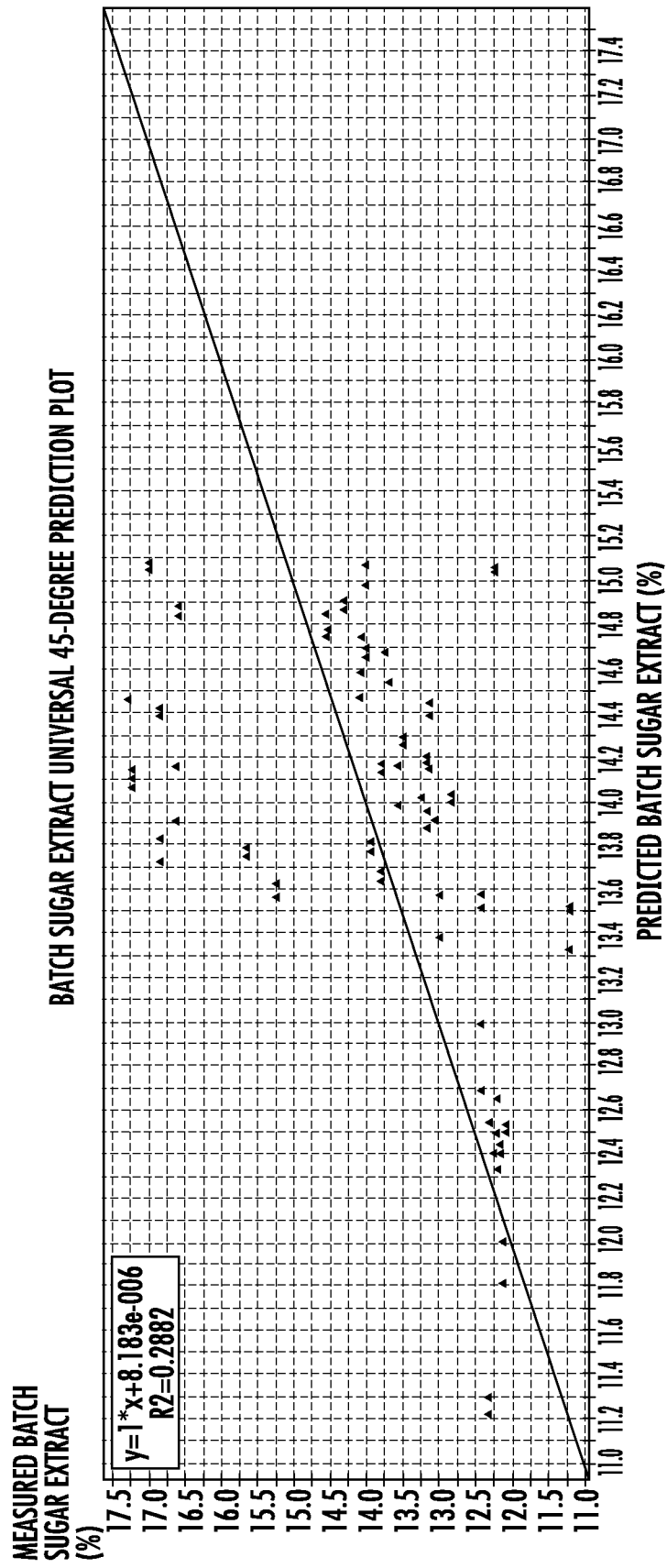
FIG. 12 is a 45-degree prediction plot graph that shows the actual measurements of sugar content from beer batches plotted against the predicted 45-degree line.
Figure 13:
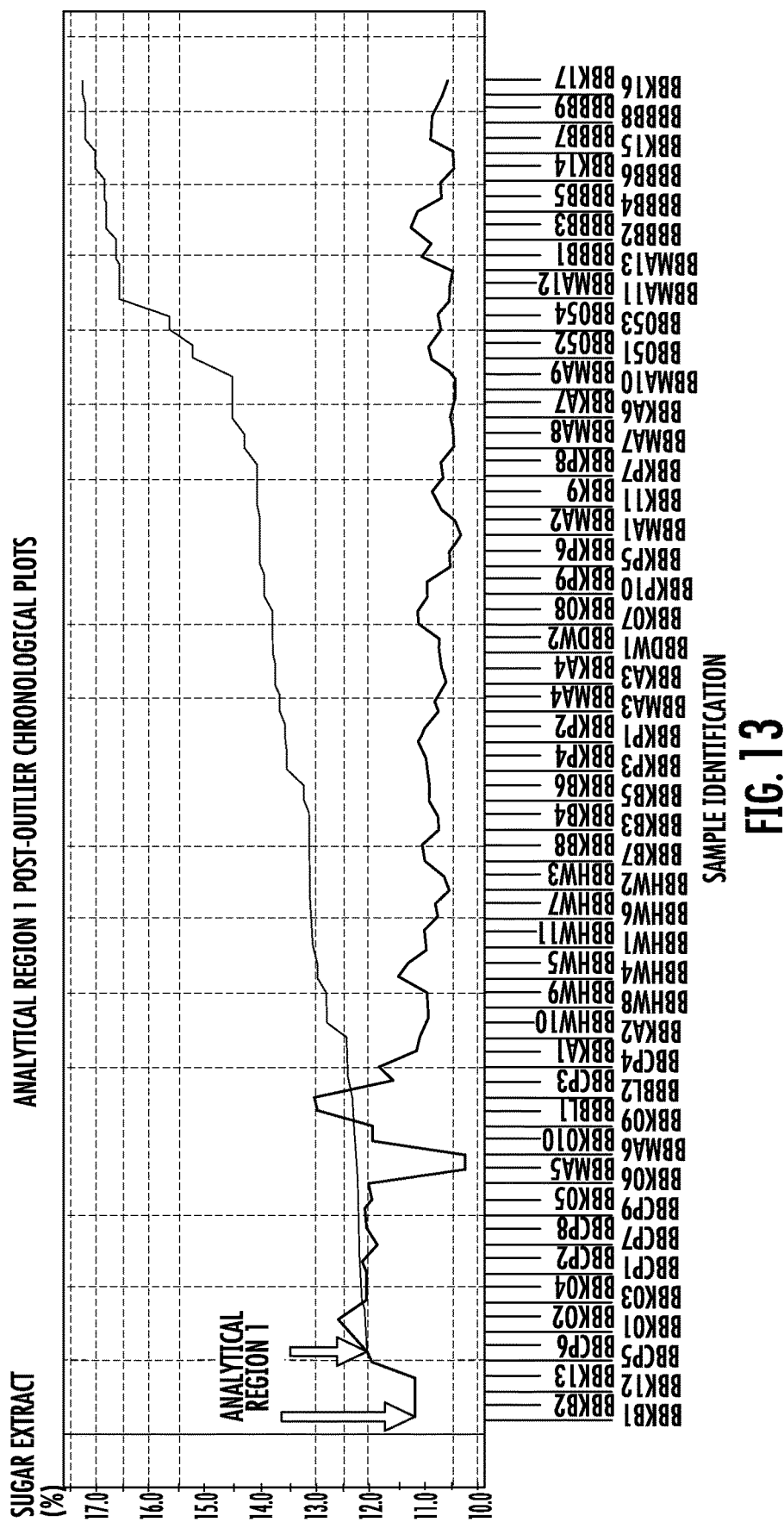
FIGS. 13-19 show actual examples of analytical regions of chronological plots examining sugar content in a batch of beer after eliminating outlier data.
Figure 14:
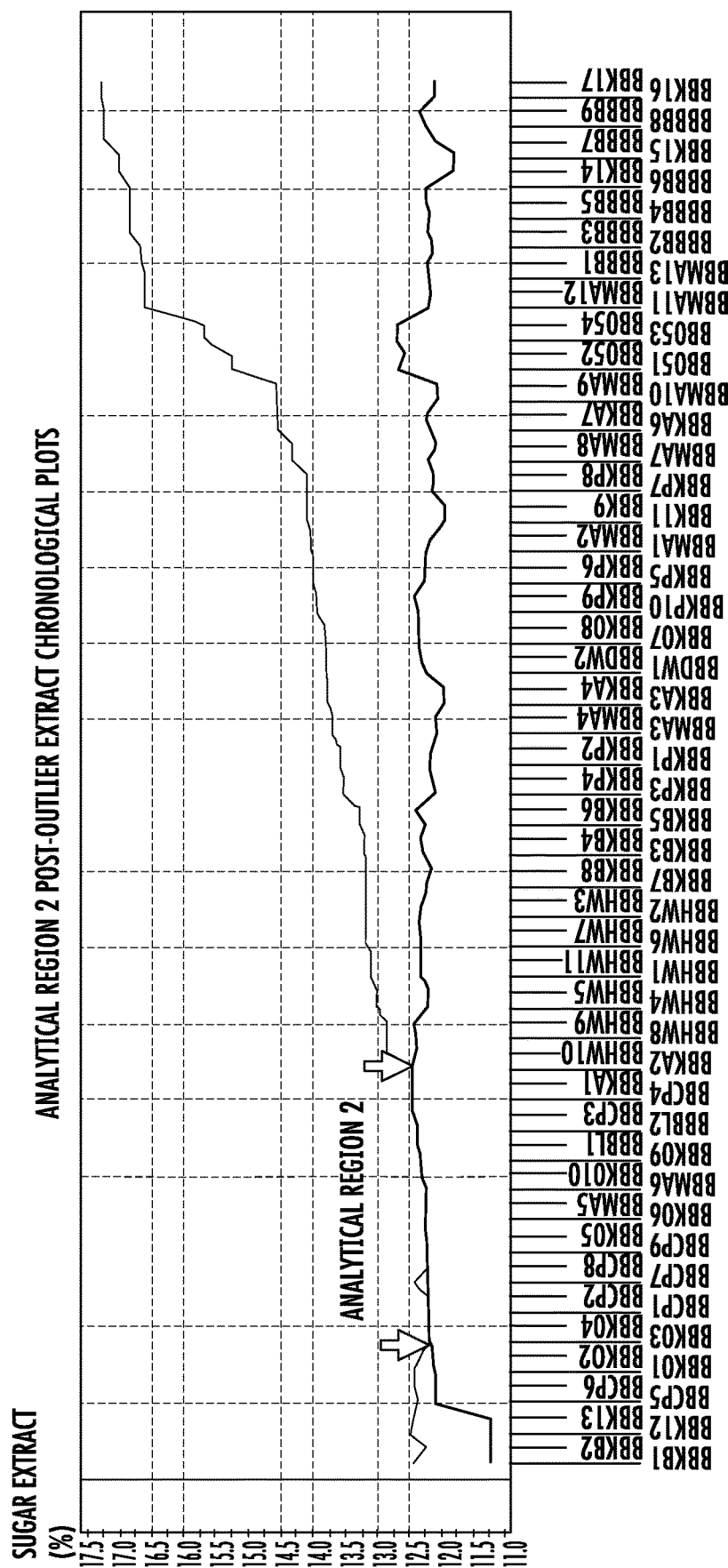
Figure 15:
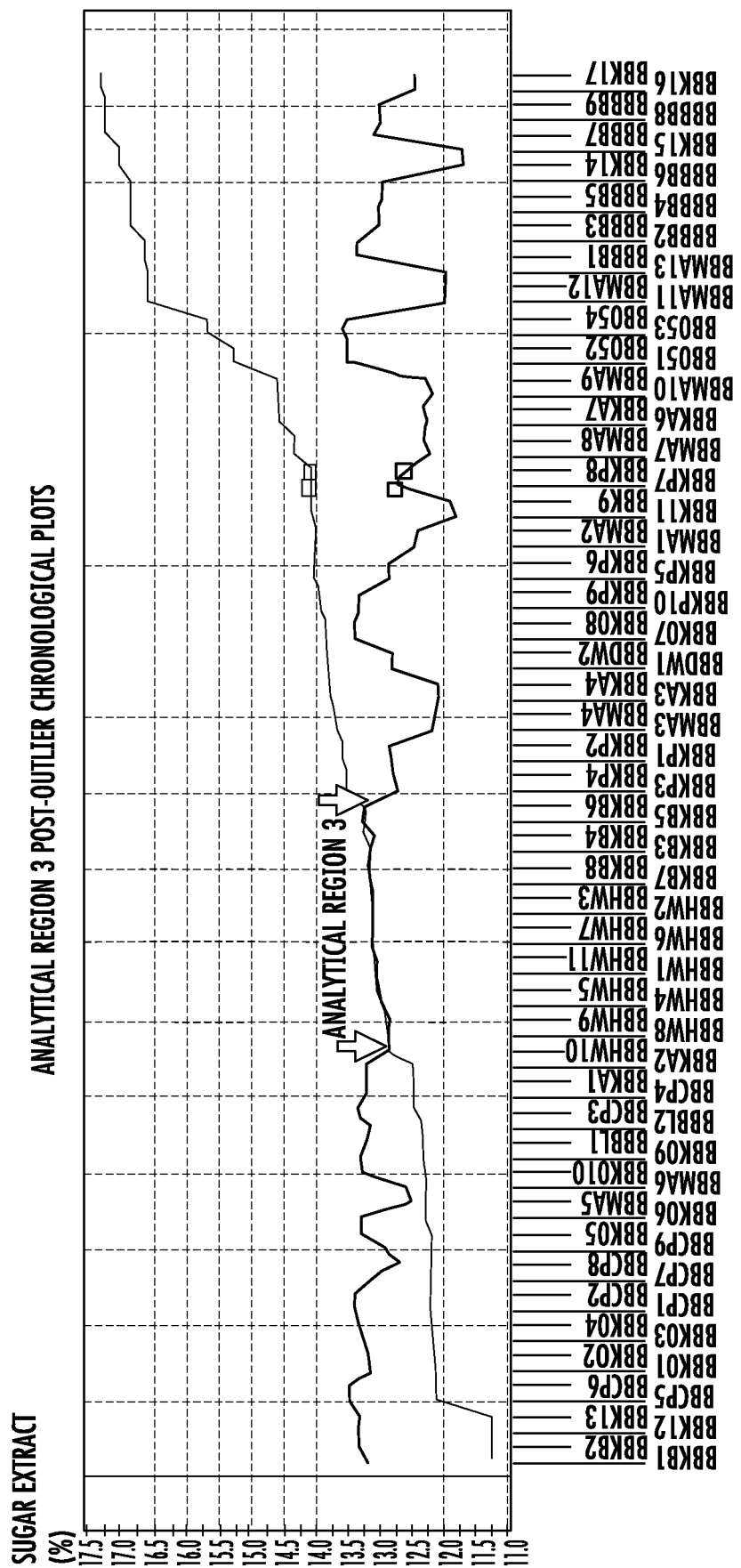
Figure 16:
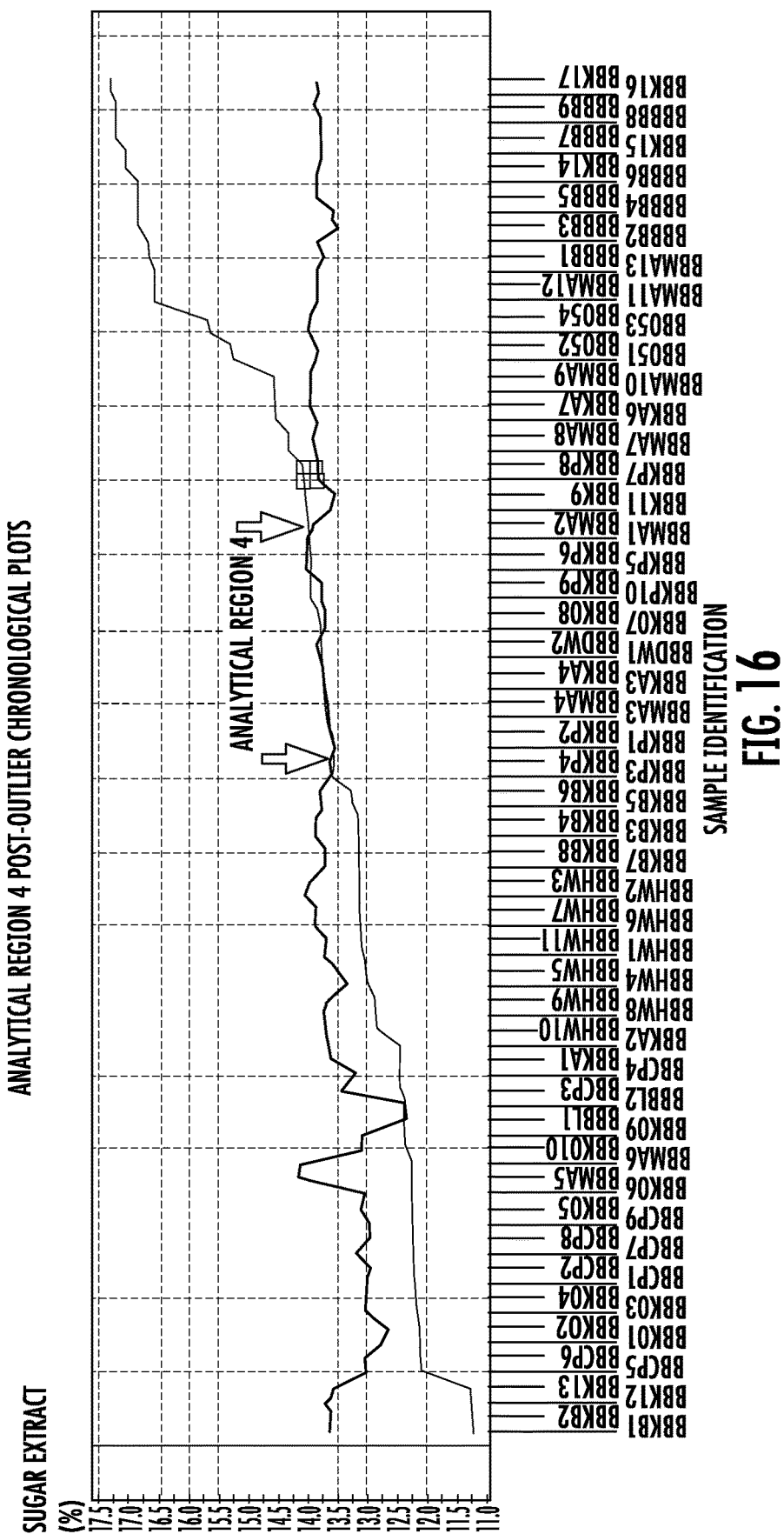
Figure 17:
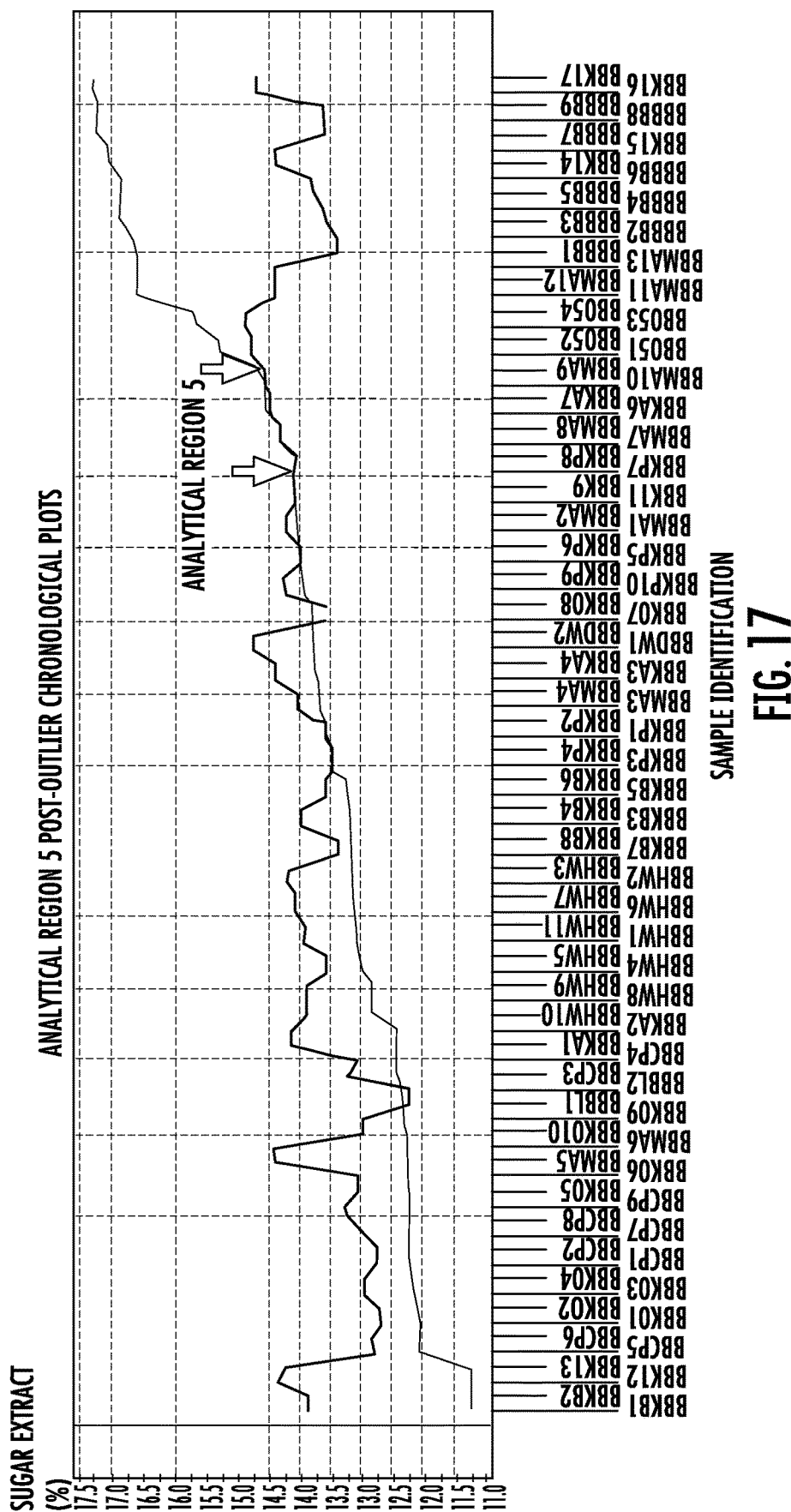
Figure 18:
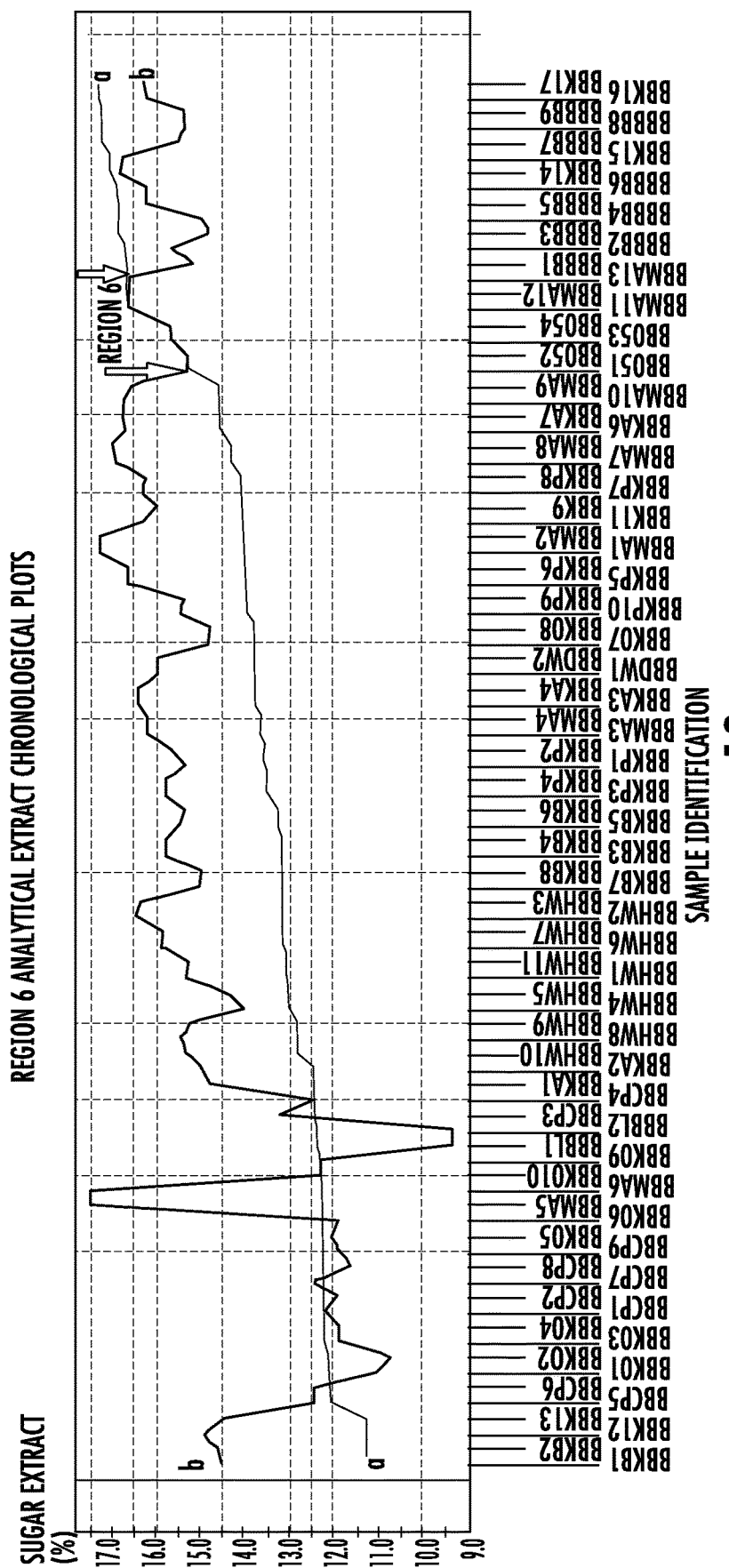
Figure 19:
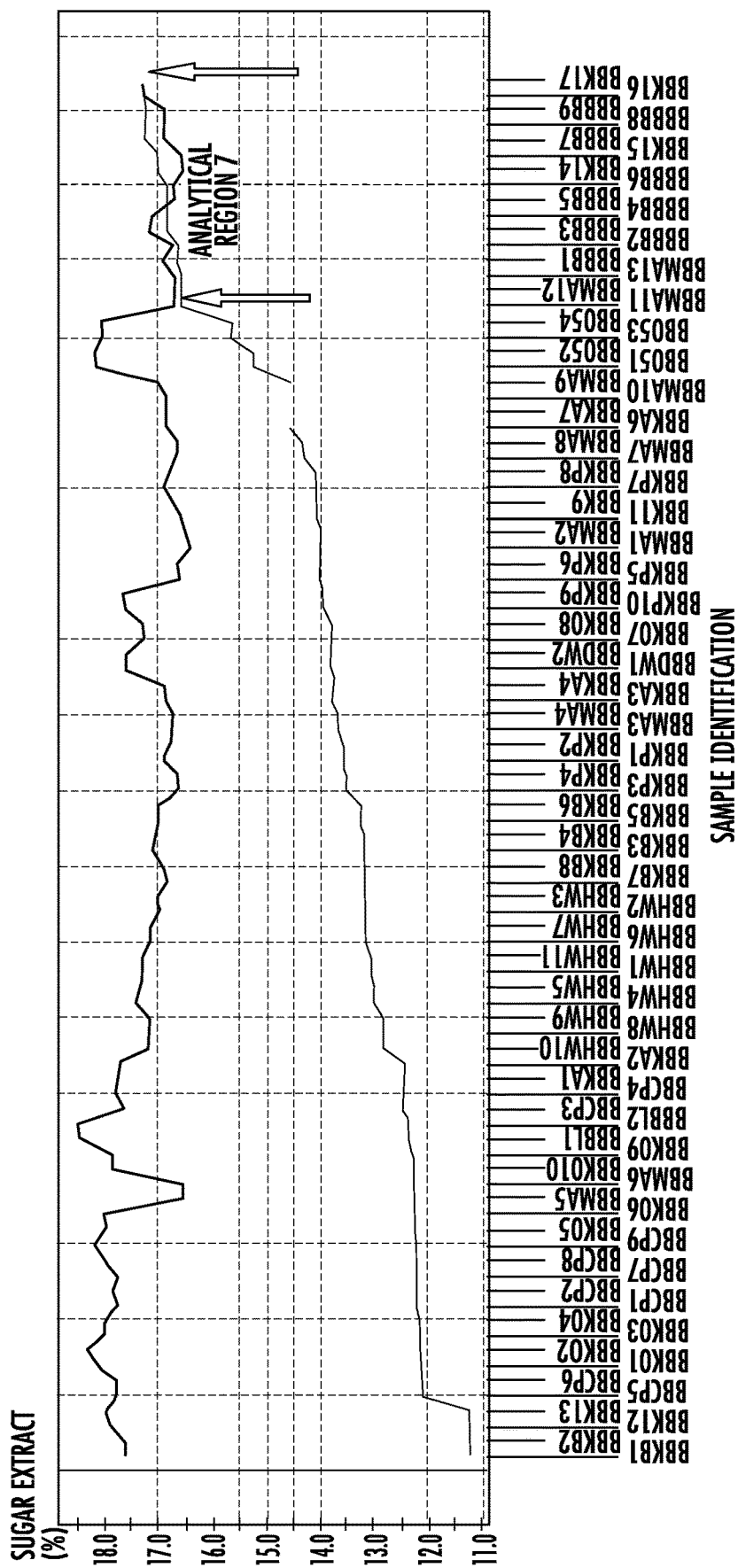

Having described the process of the analytical system, there will be described the numerical diagnostic features used in assessing the quality of our calibration and prediction models. FIG. 12 shows a 45-degree prediction plot where the geometrical shapes within the graphical plot represent the different samples analyzed.

Ideally all the samples should lie along the 45-degree line indicating a match between the reference method measured and predicted results. This may be referred to as the "45-degree Cluster Rule," which is fairly qualitative, but the numerical diagnostic feature associated with it is the Root-mean-Square Error of Prediction (RMSEP) discussed below:

$$RMSEP = \Sigma(Measured - Predicted)2/N$$

Where N is the number of sample readings.

For best prediction results from a model, as a rule of thumb, it is desirable to have a calibration and prediction model that results in the least significant digit (LSD) of the reference results overlapping with the most significant digit of the RMSEP, which shall be referred to as the "LSD Error Rule." For example, if a measured value is 12.09, then an RMSEP of 0.11 will yield a LSD error violation while a RMSEP of 0.01 will not.

In FIG. 12, the horizontal axis represents the predicted values and the vertical axis represents the measured percent sugar extract. In the specific example, the test is Sugar Extract percentage. The triangular dots in the graph represent the different samples analyzed. Ideally all the samples should lie along the 45-degree line indicating a match between the reference method measurements and the predicted results. For the best prediction results from a model, it is an aim to have a calibration and prediction model that results in the least significant digit (LSD) of the reference results overlapping with the most significant digit of the RMSEP. This "LSD Error Rule" is persistently violated as long as there are outliers in the data set although there are a few occasions where it may be mildly violated after all outliers have been removed. The universal calibration model has a Root-Mean-Square Error of Prediction (RMSEP) of 1.45 for sugar percent extract and this violates the LSD Error Rule since the measured results have their least significant digits in the hundredths place.

Figure 20:
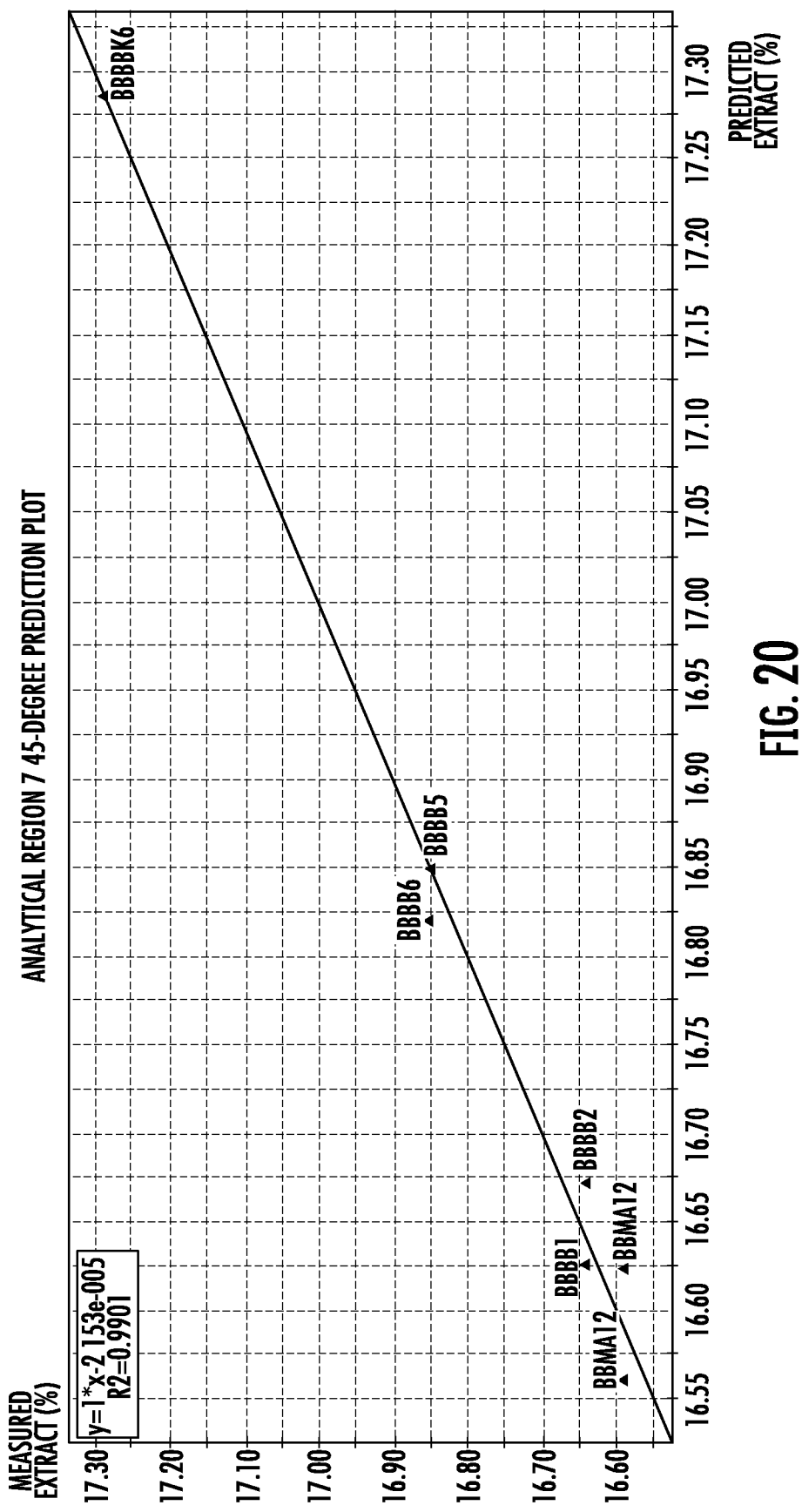
FIG. 20 is a 45-degree prediction plot graph for analytical region 7.

To improve the prediction results, the analytical system in question employs the classifier and quantifier algorithms, which segment the chronologically ordered data into linear and "quasi" linear sections and repeat the same analysis on these localized analytical regions. In this particular sugar extract example seven regions were identified. FIGS. 13 to 19 show the analytical regions 1 to 7 Chronological Plots, after eliminating outlier data using appropriate methods where applicable. FIG. 20 shows that by breaking the range down into analytical regions, the sample data more closely follows the 45-degree line for that region (analytical region 7 shown).

Figure 22:
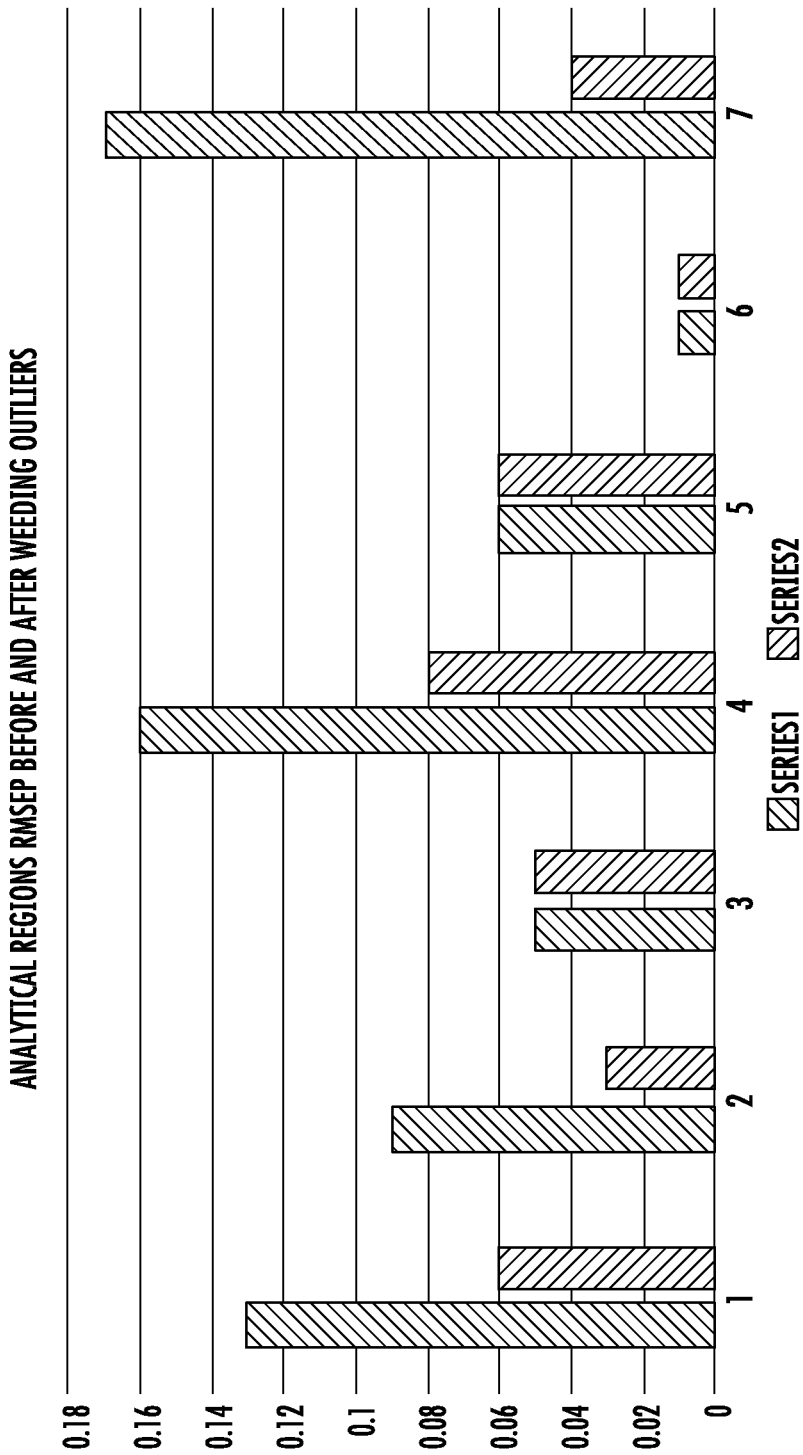
FIG. 22 is a graph representation of the data of FIG. 21.

FIG. 21 shows a summary table while FIG. 22 shows a graph that both demonstrate the RMSEP values of the seven analytical regions before (series 1) and after (series 2) the outliers have been removed. FIGS. 21 and 22 show that for four of the seven regions, the RMSEP values have been reduced significantly, thereby demonstrating that the outlier removal process can greatly improve the results.

A newly scanned or stored sample spectral data set is routed to the Classifier where the associated UCM interrogates it to ascertain the value of the parameter of interest. The determined parameter value is used to identify an analytical class of the sample.

Class discriminant equations are developed such that they assign numerical values expressing the probability of membership in the classes being tested for or neither. The discriminate equations use pre-selected wavelengths' output intensities, $\lambda_1$, $\lambda_2$ etc., and pre-assigned coefficients associated with each of the selected wavelengths, $a_1$, $a_2$ etc.

Let $c_0$ be a pre-determined constant associated with a class discriminant equation $$\text{Member Score} = c_0 + a_1\lambda_1 + a_2\lambda_2 + \ldots$$

For example:

| | Member If | Borderline Member If | Not a Member |
|---|---|---|---|
| Member Score (MS=) | .65 <= MS <= 1.35 | .35 < MS < .65 | MS > 1.35, MS < .35 |

FIG. 24 demonstrates an example of the membership determination output that is based on the analytical class cut off points of FIG. 23.

The Quantifier will precisely predict the parameter value (PV) of interest of a sample by evaluating the equation that utilizes the spectral intensity output from pre-selected wavelengths as shown below.

$$PV = b0 + o1\lambda 1 + o2\lambda 2 + \ldots$$

where
b0 is a pre-determined constant
λi are pre-determined wavelengths, and
Oi are the spectral intensities at the preselected wavelengths.

The prediction equations stored in the library will have the format shown above, even though some of them may have higher order terms such as quadratic, cubic etc. For example, if the equation for % Alcohol has:
$b_0 = 3$
$o_1 = 5$
$o_2 = 6$
then $$\% \text{ Alcohol} = 3 + 5\lambda_1 + 6\lambda_2$$

When a sample is spectroscopically scanned the system will retrieve the intensities associated with wavelengths $\lambda_1$, e.g. 550 nm, and $\lambda_2$, e.g. 622 nm, and input, and evaluate the parameter, e.g. % Alcohol, from these measurements.

A specific embodiment of the invention will now be described with reference to FIGS. 25 to 32 and to a beer brewing application, though the person skilled in the art will readily understand that the methods and interfaces described can be applied to many different applications, including standardized and non-standardized processes. A standardized process is considered to be a process that follows a well established series of process steps, though variations within these process steps may be possible.

A user may pre-register for an account with an online analysis lab. The user may enter into a payment plan with the online analysis lab. For example, the user may pay a fixed amount per month or may pay on a per-use or other basis. The user's payment may entitle the user to a number of analysis services, a period of analysis services, or a combination. Specific registration and payment plans are not considered pertinent to the present invention and with online registration systems being well established for many internet-based services, no further description of the registration process is considered necessary herein.

Figure 25:
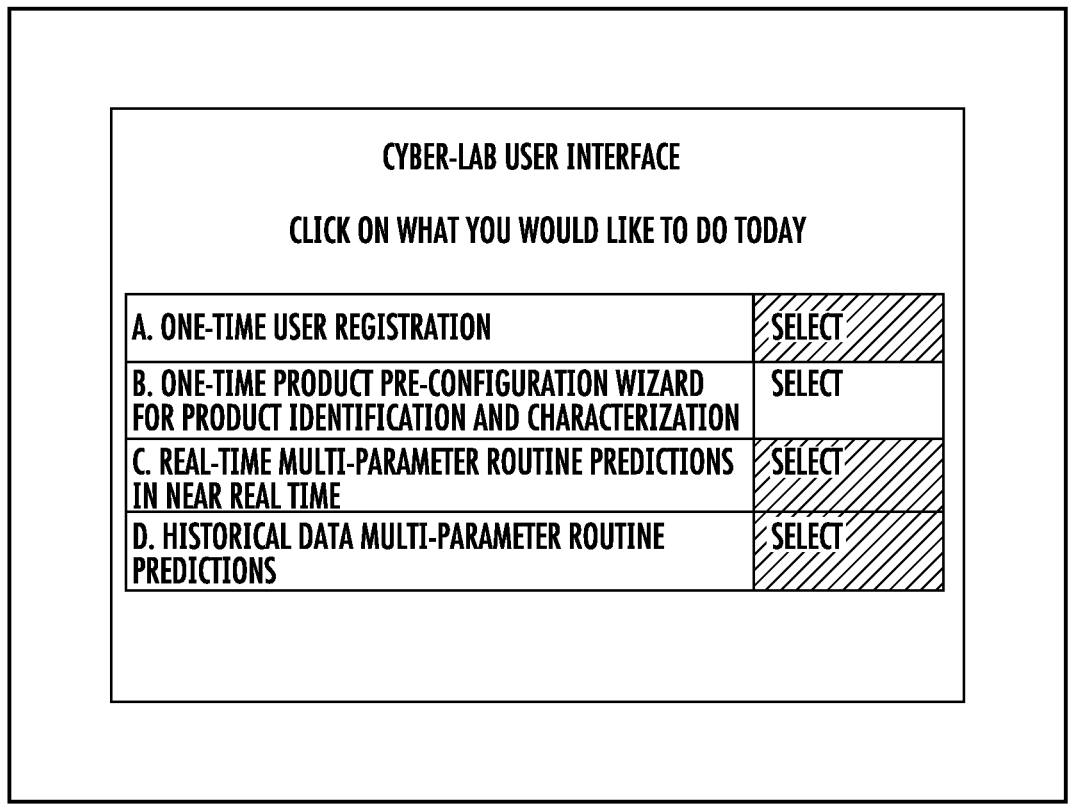
FIG. 25 shows a welcome interface for the online analysis lab.

After logging in to the online analysis lab, the user may be presented with a welcome interface, of which a simple configuration is demonstrated in FIG. 25. The welcome interface may prompt the user to highlight and select, e.g. by cursor selection, key toggles, or touchscreen, one of the available options. In the example depicted, the available options include a One-time User Registration, One-time Product Pre-configuration Wizard, Real-Time Multi-parameter Routine Predictions and Historical Data Multi-Parameter Routine Predictions.

If the user selects the One-time Product Pre-configuration Wizard, the user may be taken to an initial wizard interface as shown in FIG. 26 where the user is prompted to select a particular industry application. The options listed in the interface of FIG. 26 include wine, beer brewing and dairy though any other industrial process may be represented. Furthermore, the product pre-configuration may have categories to enable a user to navigate to the particular industry required. For example, wine, beer brewing and dairy may all be within a higher "food and beverage" category. A search feature may be provided to enable a user to search on the available industries.

In the present example, the user selects beer brewing and is taken to the next stage of the pre-configuration wizard, as shown in FIG. 27, which informs the user of the available stages of the brewing process at which the analysis can be performed and the parameters that can be measured.

As shown in FIG. 28, the user is then presented with an interface screen that prompts the user to select which of the available processes the user would like to pre-configure. After each selection, the user may be presented with an interface as shown in FIG. 29, which informs and prompts the user for information pertaining to the expected range of results for the given parameter, which in the present example, is the Sugar Original Extract (%) (PEO). Sample ranges may be presented for the information of, and selection by, the user as shown in FIG. 30. The user is able to enter expected ranges for each product's parameters previously determined by the user using any suitable reference method.

The online analysis lab cycles through the screens of FIGS. 28 and 29 until data for each parameter and each process stage has been entered.

If at the welcome screen of FIG. 25, the user selects Real-Time Multi-parameter Routine Predictions, the user is taken to a sampling wizard that guides the user through the process for obtaining and transmitting a sample. The user is prompted to enter samples into the probe sensor which then samples the data and uploads the data to the online analysis laboratory. The user is prompted to enter a file name for the uploaded data so that the data may be stored in associations with the user's account on the online system.

The user can then validate and predict the results for the data. This stage can also be selected through the Historical Data selection of the interface of FIG. 25 by retrieving a previously stored file. FIG. 31 shows a validation screen after execution of the classification process described above. The validation screen indicates whether the range of values for a parameter are within the pre-configured expected ranges. Specific values for the validated parameters can then be predicted by retrieving the appropriate equations for the parameter and using the data and classifications to predict a precise value for the parameter. The final output screen (FIG. 32) may show a summary of the results, including an output range column and a results column which shows the precisely predicted value. The results summary interface can also summarize the user's account credit, provide options for receiving/storing the results and options for further analysis of other samples.

Figure 33:
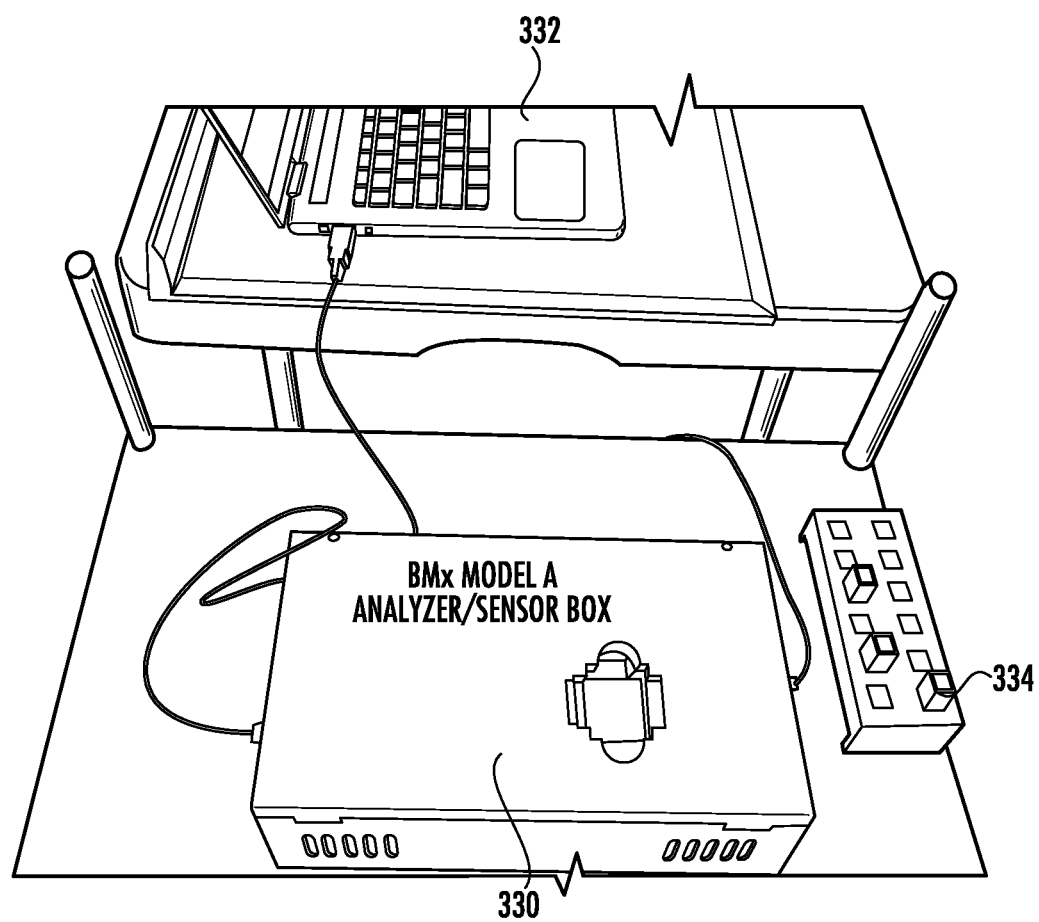
FIG. 33 shows a system for virus detection.

FIG. 33 shows actual sample apparatus for an embodiment of a virus test system in accordance with the present disclosure. The system includes a BMx Model A Analyzer/Sensor Box 330, a computer with access to the internet 332 and disposable cuvettes 334. The computer system may be programmed with a BMx analytic software. Test Subscription that enables sample data to be uploaded and processed in real-time to generate a result on the sample.

The Sensor Box and the computer do not have to be in proximity as shown in the figure. They can be as far part as possible, or even in different rooms/cubicles, depending on the length of the USB cable used. In addition, wireless connectivity between the sensor and the computer may be implemented.

Figure 34:
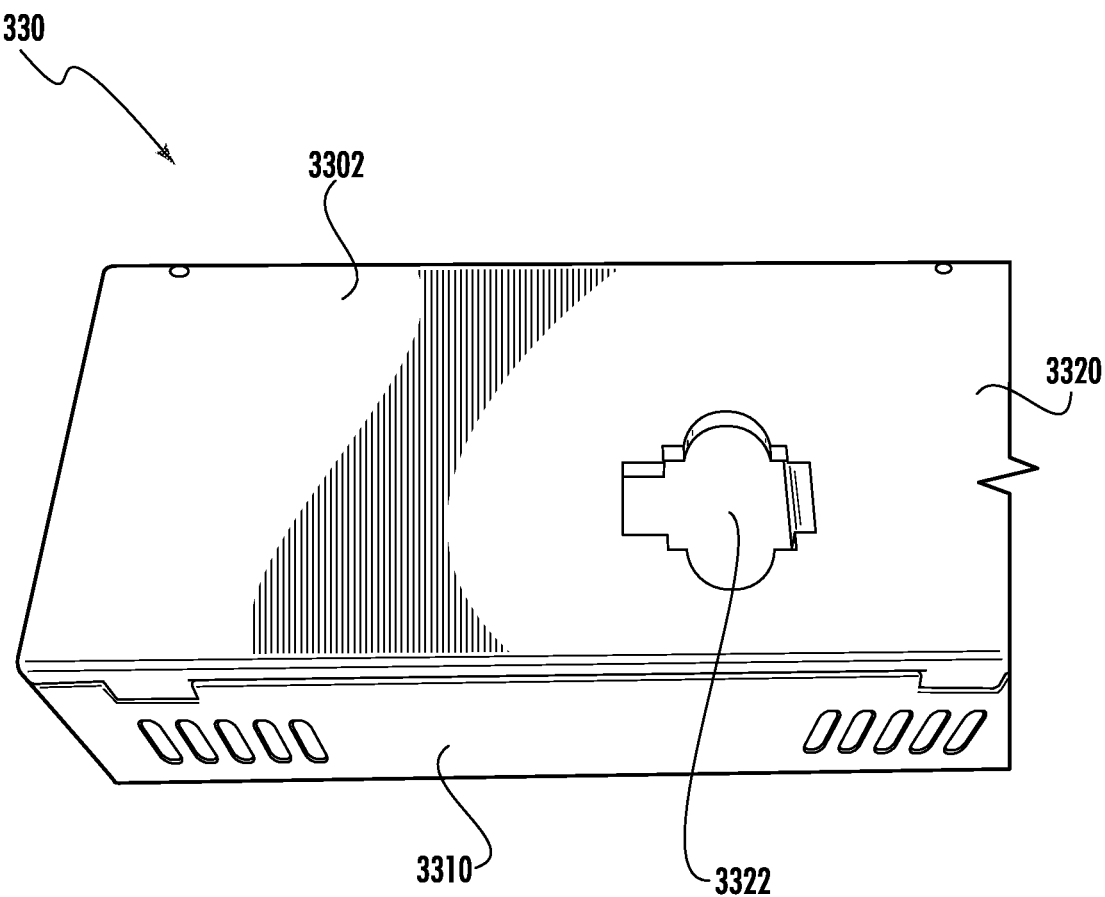
FIG. 34 shows an embodiment of a sensor box.
Figure 35:
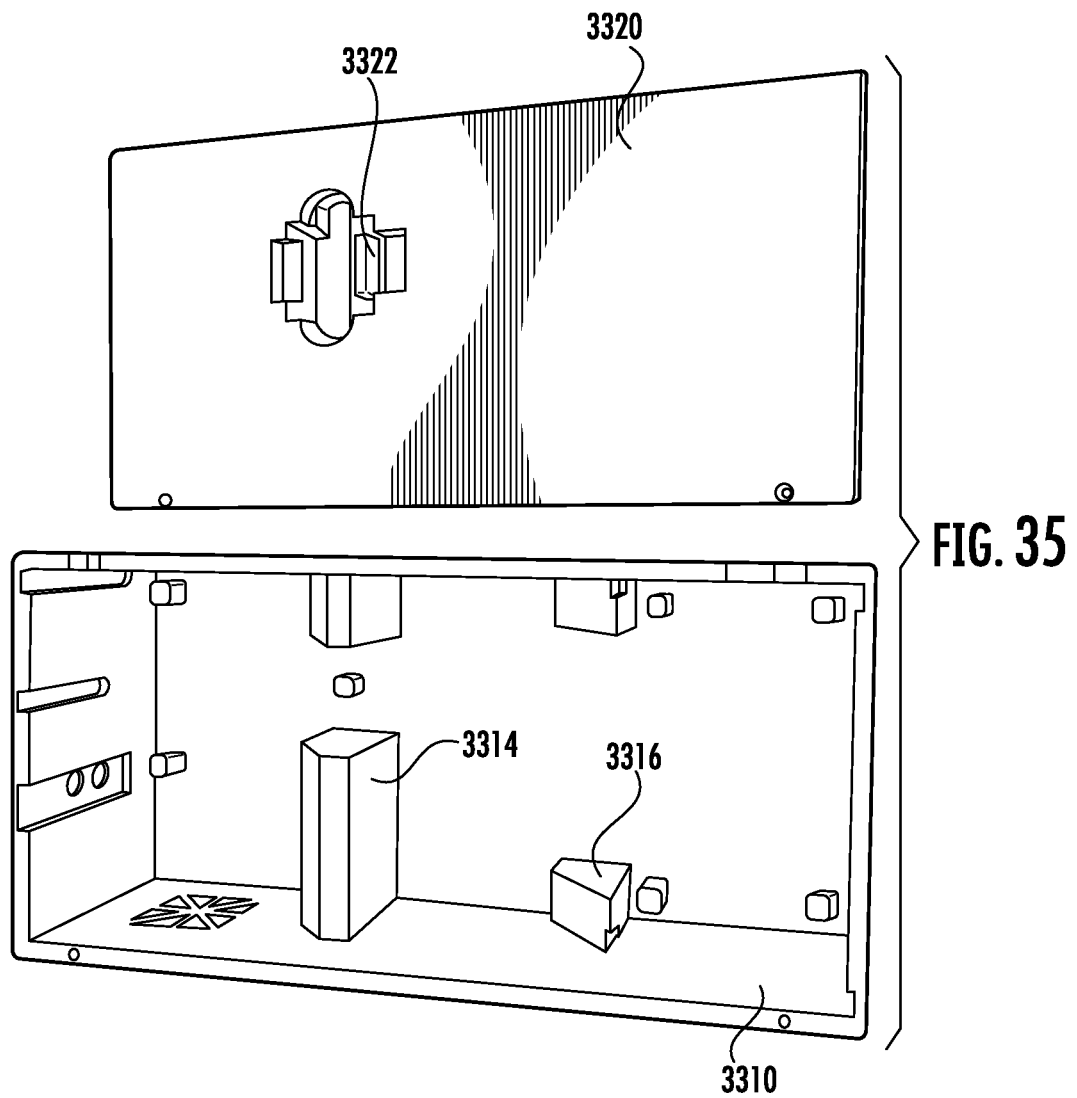
FIG. 35 shows an embodiment of a housing for a sensor box.
Figure 36:
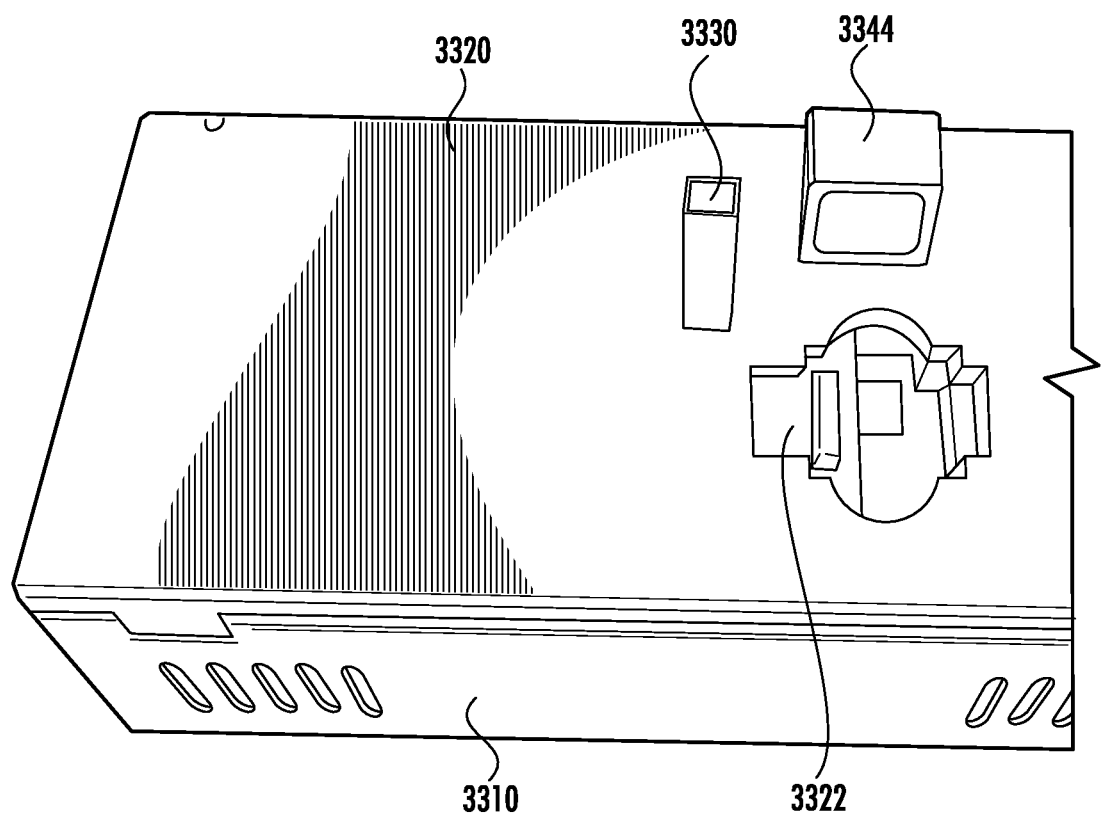
FIG. 36 shows a cuvette and cover that can be used with the sensor box.

FIG. 34 shows an embodiment of the sensor box 330 for receiving and analyzing samples. The sensor box 330 includes a housing 3302. The housing 3302 includes a chassis 3310 and a lid 3320 (FIG. 35). The chassis 3310 is considered a drop and stick chassis with internal formations (e.g. projections, slots, recesses, and divisions, such as projections 3314, 3316) that are configured to receive and hold the components of the sensor box. The chassis lid 3320 may be secured to the chassis 3310 by any suitable means including a hinge joint (as shown), screws, latches, press fit detents, etc. or a combination of such methods. The chassis lid 3320 includes a sliding cover 3322 that can slide open to provide access to a sample chamber or slide closed to cover the sample chamber and prevent ambient light from entering the sample chamber. When open, as shown in FIG. 36, a cuvette 3330 containing a sample may be inserted into a sample holder (described below) within the sensor box 330. A cuvette cover 3344 may be placed on the sample holder to encase the cuvette containing the sample. The chassis 3310 and chassis lid 3320 may be 3-D printed, plastic molded or formed by any other suitable processes.

Figure 37:
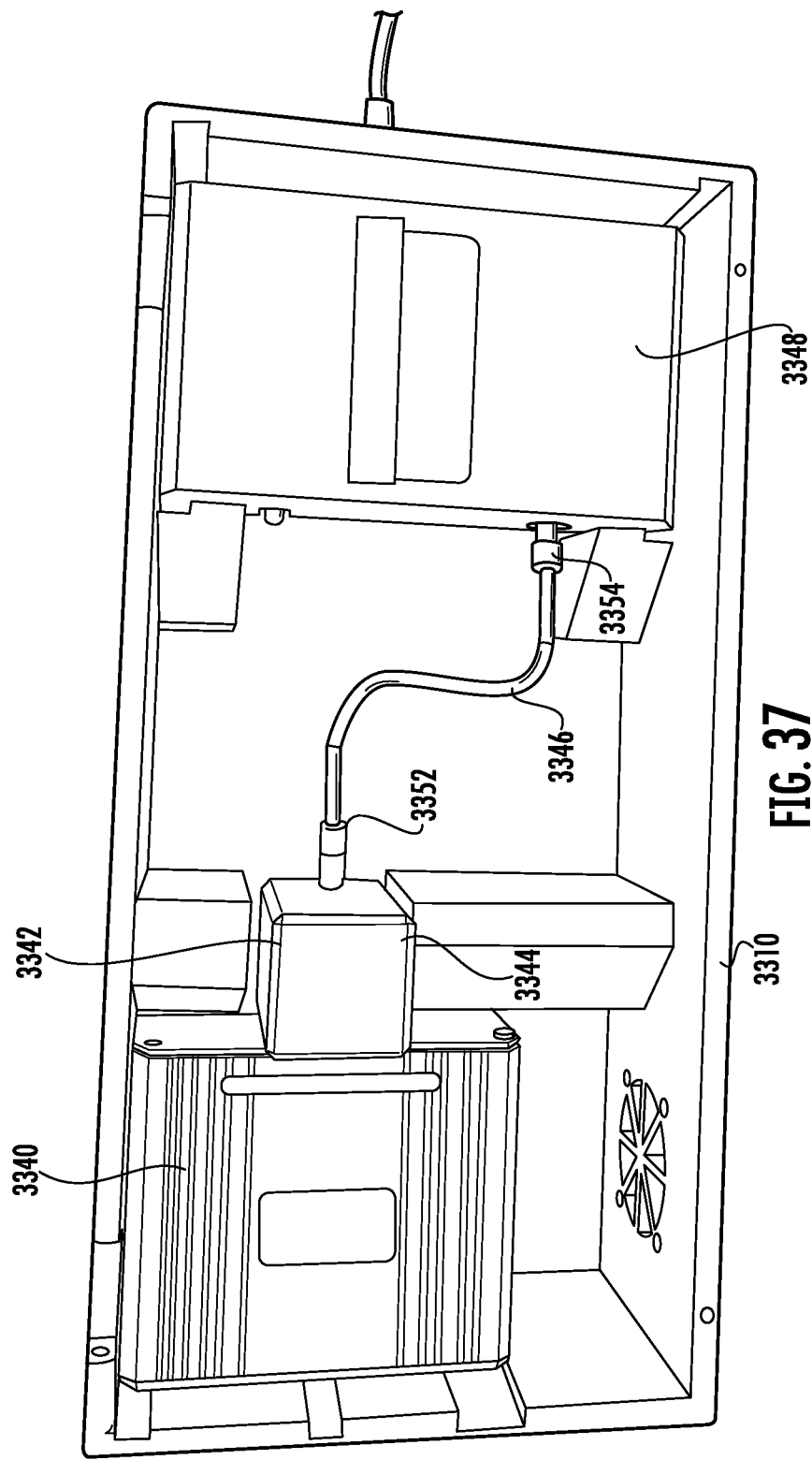
FIG. 37 shows an embodiment of the internal components of the sensor box.
Figure 38:
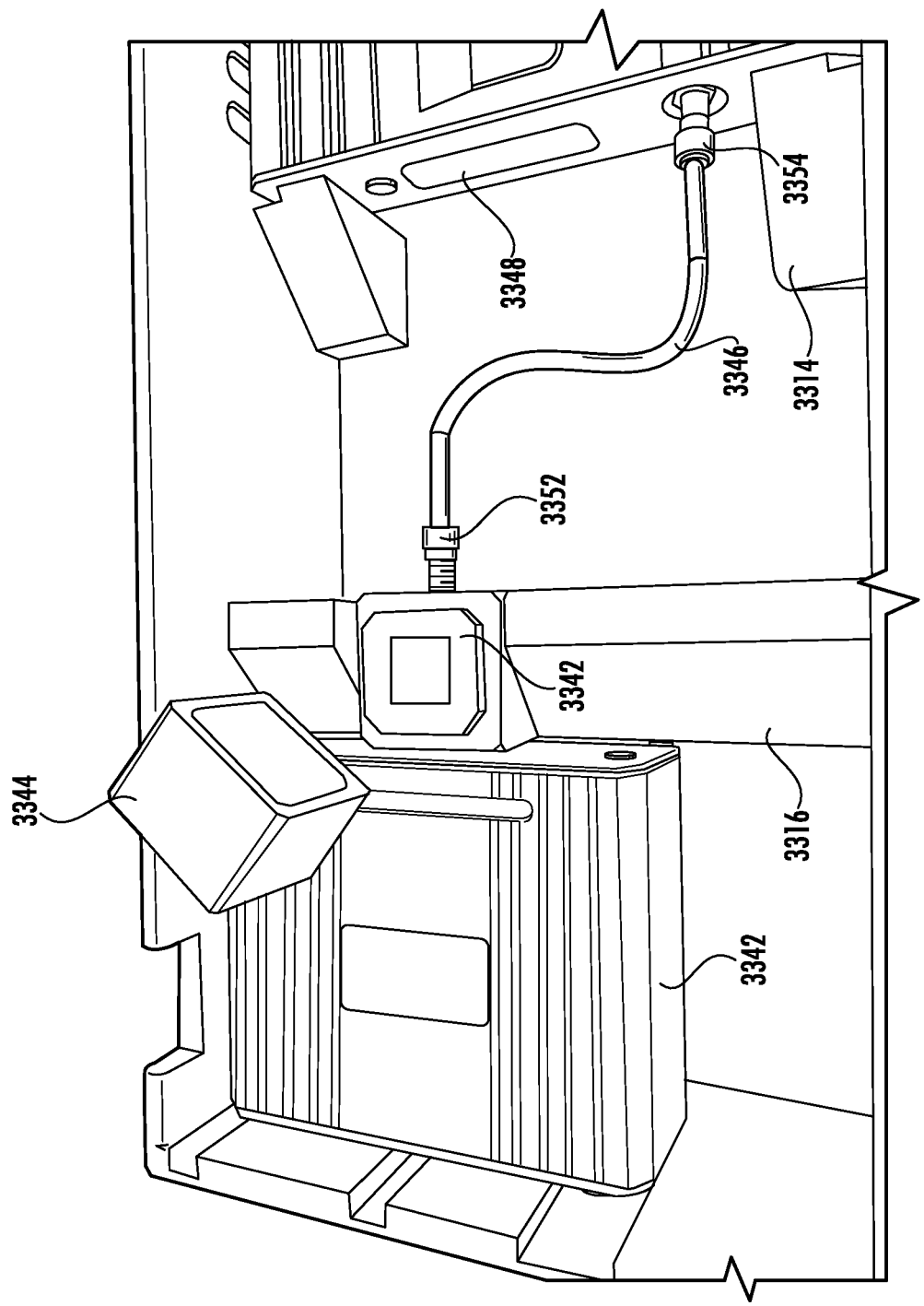
FIG. 38 shows the internal components of the sensor box with a cover removed from a sample holder.

As stated above, the chassis 3310 includes internal formations (e.g. projections, slots, recesses and divisions) that are able to receive and secure the components of the sensor box 330. FIG. 37 shows an internal view of the chassis 3310 including the working components of the sensor box 330. The sensor box 330 includes an AC powered lamp 3340, a sample holder 3342 that receives the cuvette 3330 containing a sample, cuvette cover 3344, optical fiber 3346 and spectrometer 3348. The internal formations within the chassis 3310 allow for precise fit of these components thereby removing or at least minimizing the need for additional fastenings, such as screws. However, additional fasteners can be utilized if preferred. FIG. 37 shows the sample holder 3342 with the cuvette cover 3344 in place. FIG. 38 shows the sample holder 3342 with the cuvette cover 3344 removed to enable the sample holder 3342 to receive a cuvette 3330.

The sample holder 3342 includes an aperture (not shown) in one side of the sample holder 3342. The lamp 3340 abuts the sample holder 3342 so that light is projected directly from the lamp 3340 into the sample holder 3342 within minimal stray light from the lamp 3340 escaping into the chassis cavity. Thus, light from the lamp can illuminate a sample within a cuvette located in the sample holder. An inlet end 3352 of the optical fiber 3346 connects to an opposite side of the sample holder 3342 from the lamp 3340. An outlet end 3354 of the optical fiber 3346 connects to the spectrometer 3348. Thus, the optical fiber 3346 is able to conduct light that has passed through a sample within the sample holder 3342, and is thus encoded with the sample wavelength signature, from the sample holder to the spectrometer 3348 for analysis by the spectrometer 3348.

As stated above, the lamp 3340 may emit light across a range of wavelengths in in the visible and near infrared. In one embodiment, the lamp 3340 may be a halogen lamp that emits light in the wavelengths 400 to 1100 nm. In one embodiment, the spectrometer may be a BLUE-Wave™ spectrometer available from StellarNet Inc.

Figure 39:
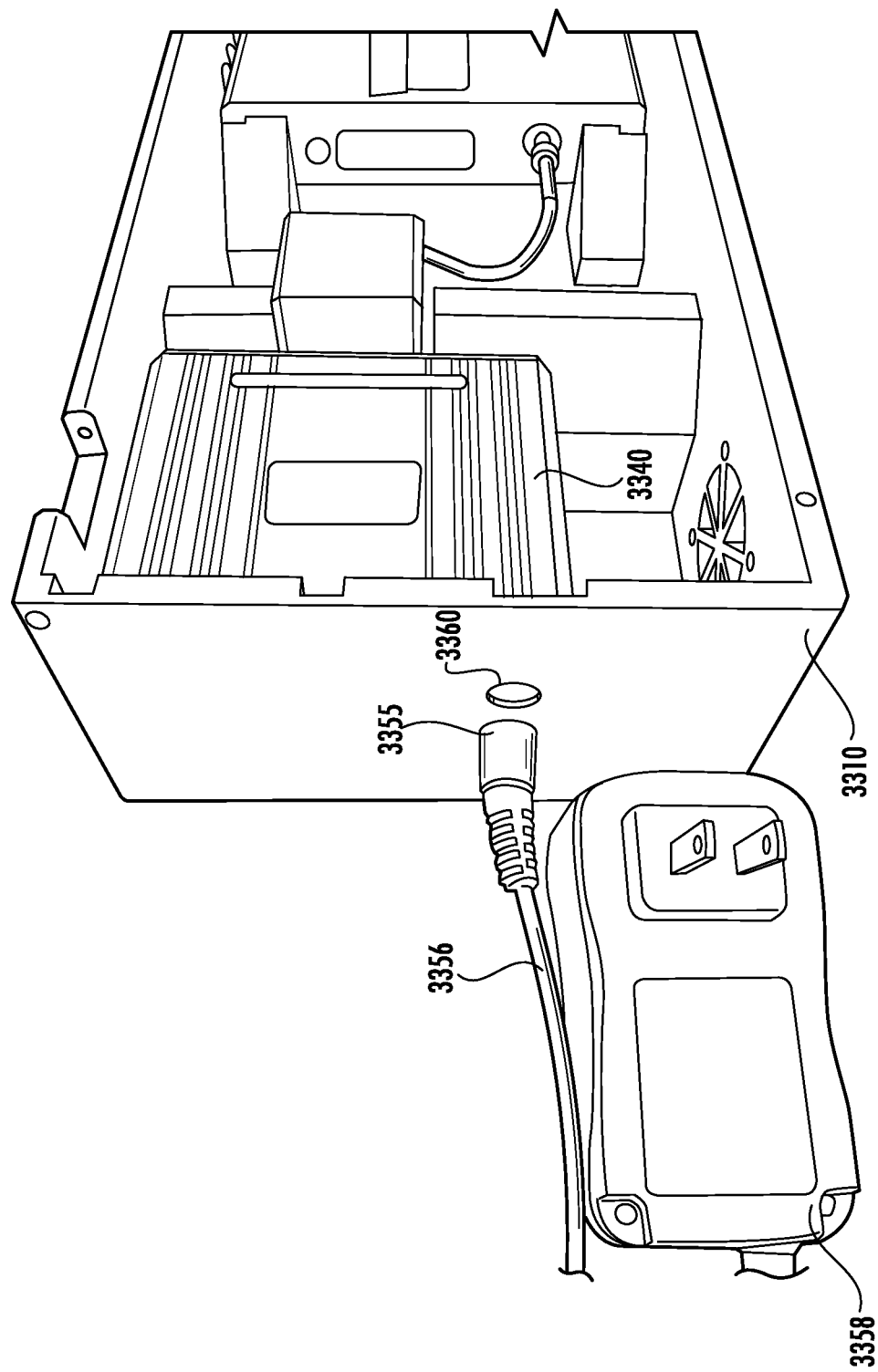
FIG. 39 shows a power supply for the sensor box.

The lamp 3340 includes an inlet power port and a switch on one side of the lamp. As shown in FIG. 39, the chassis 3310 may be provided with an aperture 3355 that allows a connection of a power cable 3356 for a power supply 3358. A further aperture 3360 may provide access to the lamp switch.

Figure 40:
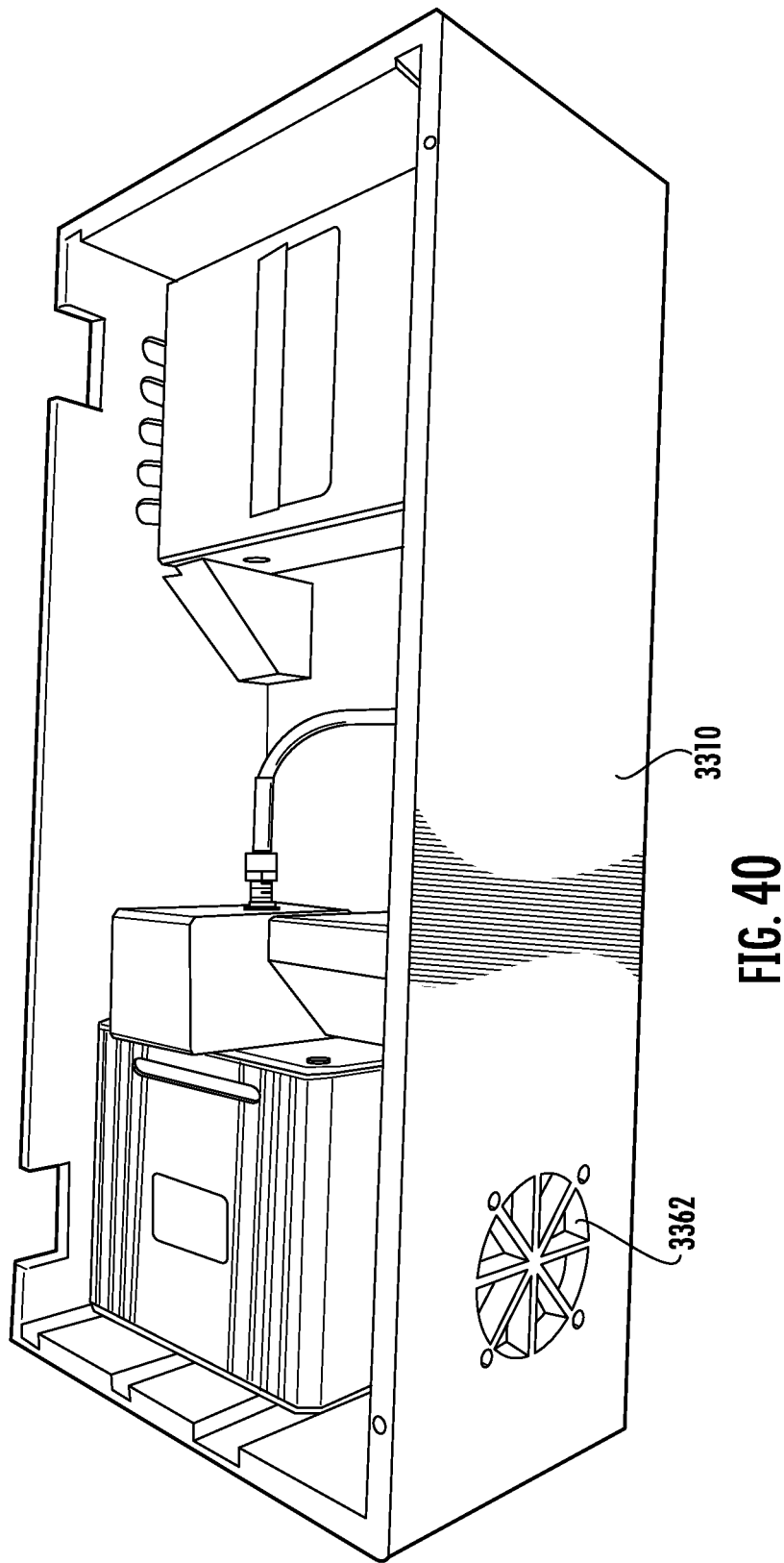
FIG. 40 shows a fan port of the sensor box.
Figure 41:
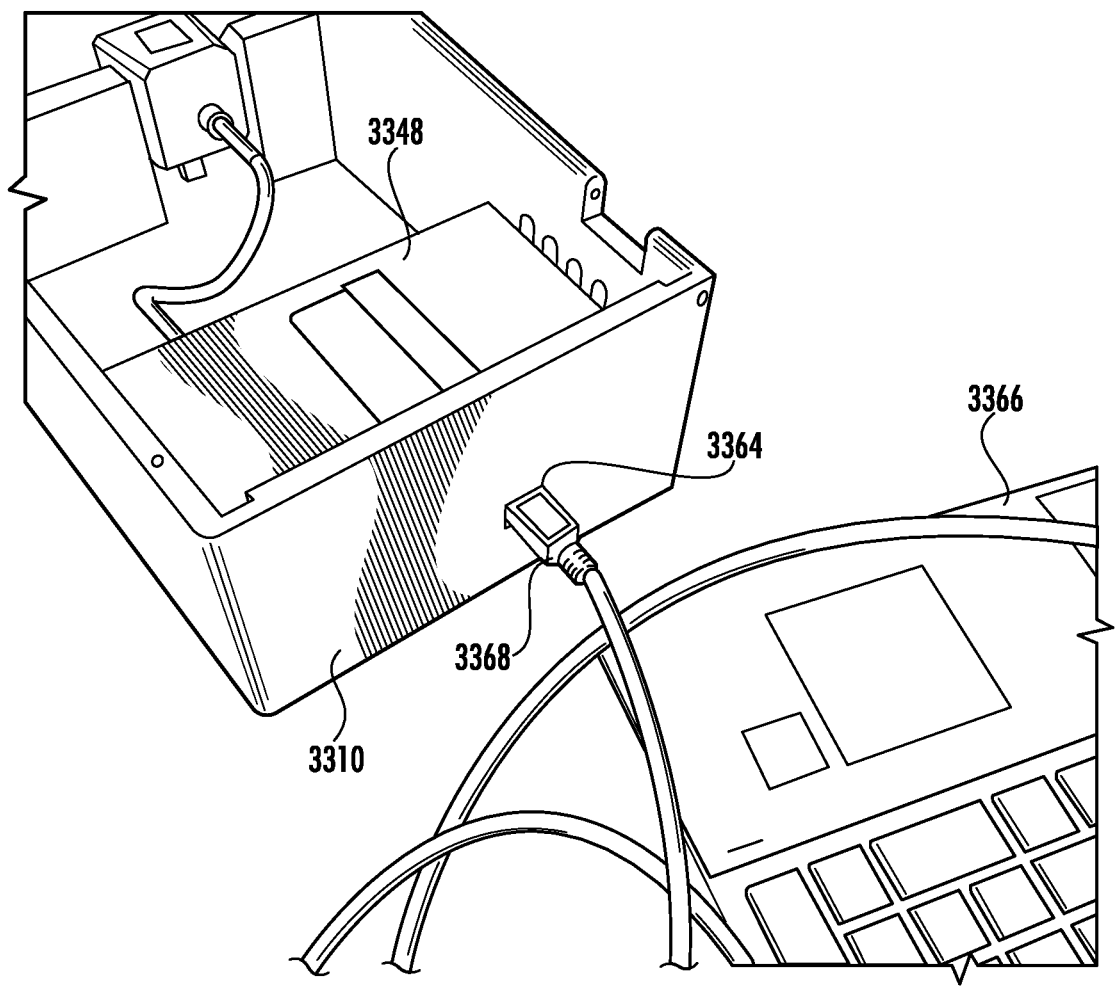
FIG. 41 shows a data port of the sensor box.

On a side of the chassis 3310, there may be provided a fan port 3362 (FIG. 40). A fan (not shown) may optionally be provided adjacent to the lamp 3340 for cooling the lamp and other components.

In the chassis 3310 adjacent the location of the spectrometer 3348, a data port 3364, such as a USB port, allows a connection of the spectrometer 3348 to an external computer 3366 via a cable 3368. A computer may be used to extract data from the spectrometer and to execute analysis programs. A USB connection can also be used to provide power to the spectrometer.

Figure 42:
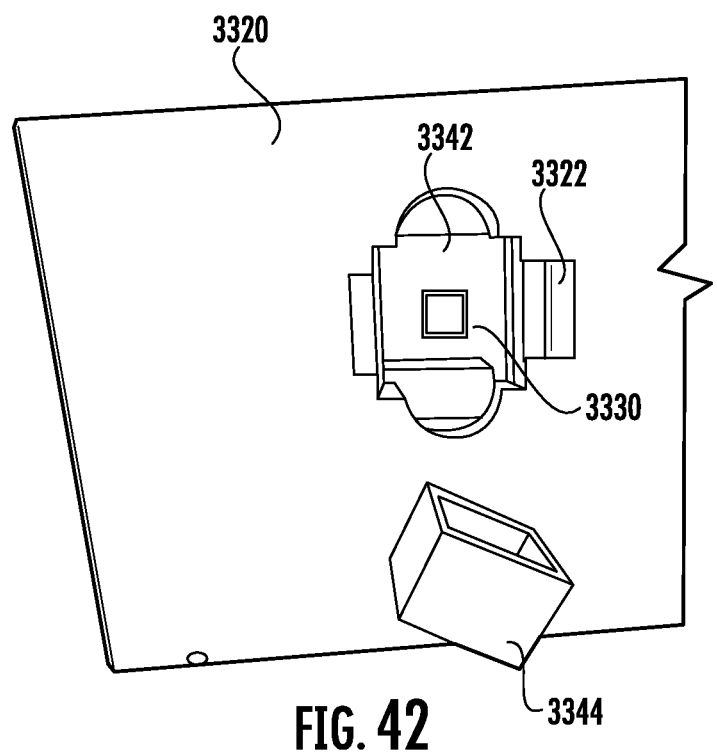
FIG. 42 shows a first step of loading the sensor box.
Figure 43:
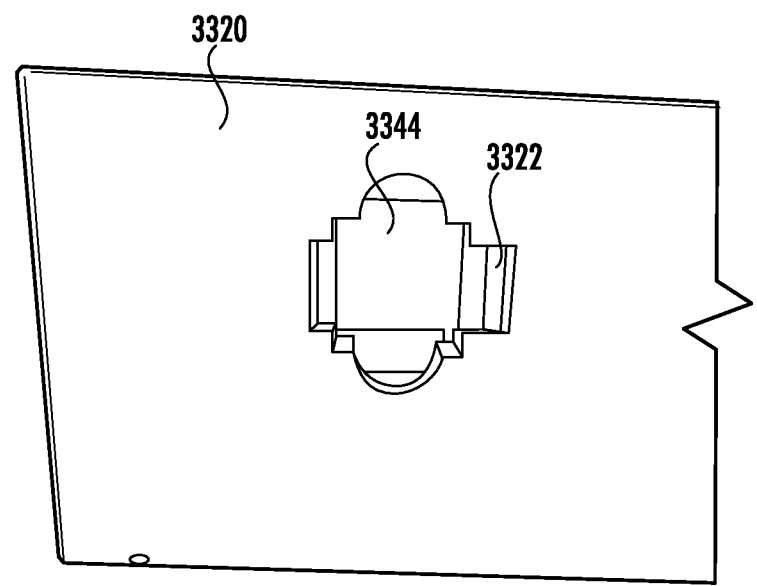
FIG. 43 shows a further step of loading the sensor box.
Figure 44:
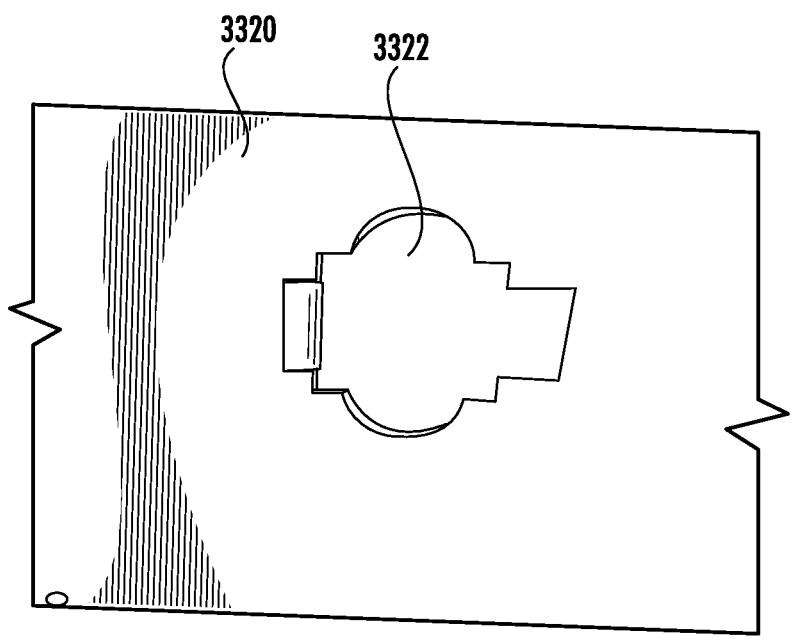
FIG. 44 shows a final step of loading the sensor box.

The sensor box may be operated by first placing a liquid sample in the cuvette 3330 and then locating the cuvette into the sample holder 3342 (FIG. 42). The cuvette cover 3344 may then be placed over the cuvette to seal the sample holder 3342 from ambient light within the chassis (FIG. 43). The sliding lid 3322 may then be closed to seal the sensor box 330 from external light (FIG. 44).

Figure 45:
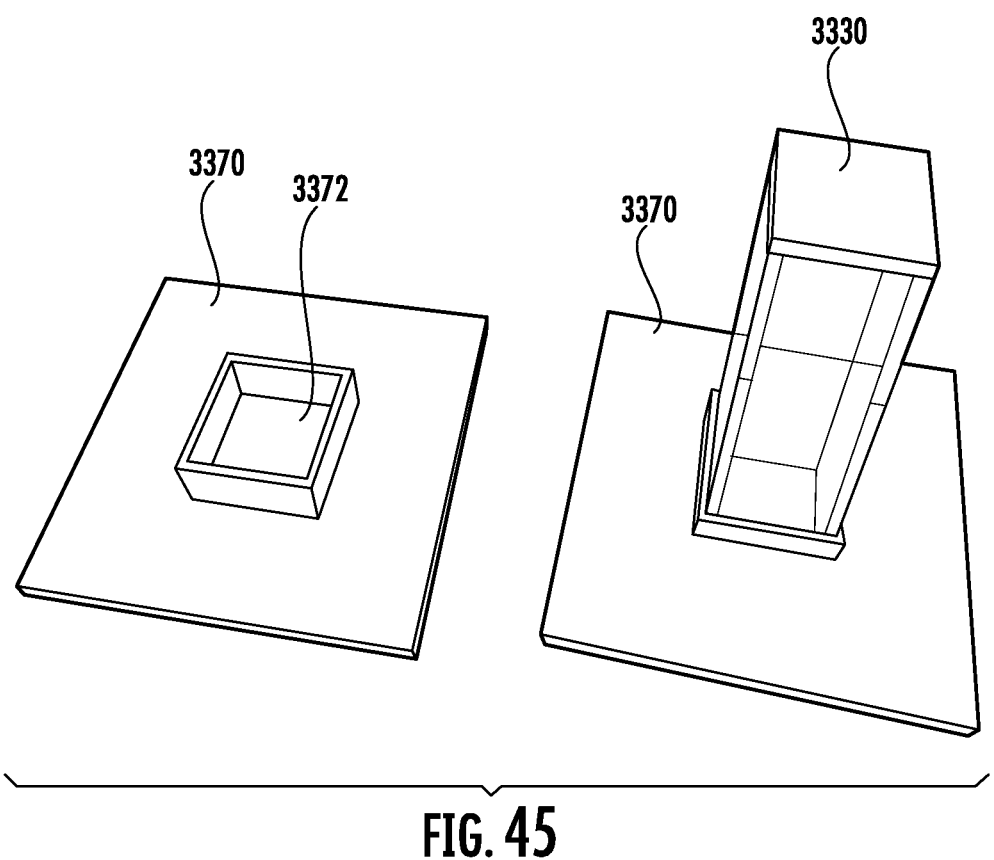
FIG. 45 shows a sample holder in isolation and a sample holder holding a cuvette.

FIG. 45 shows the sample holder 3342 in more detail, including its engagement with the cuvette 3330. The sample holder 3342 includes a base 3370 with a square aperture 3372 that receives a square-based cuvette 3330. The cover 3344 is located over the base and encases the cuvette. Typical cuvettes are round bottomed and fall over easily, or must be supported in a cuvette rack to prevent spectrometer sample spills on work benches. By contrast, the cuvette 3330 is square bottomed and designed specifically for interaction with the sample holder.

Figure 46:
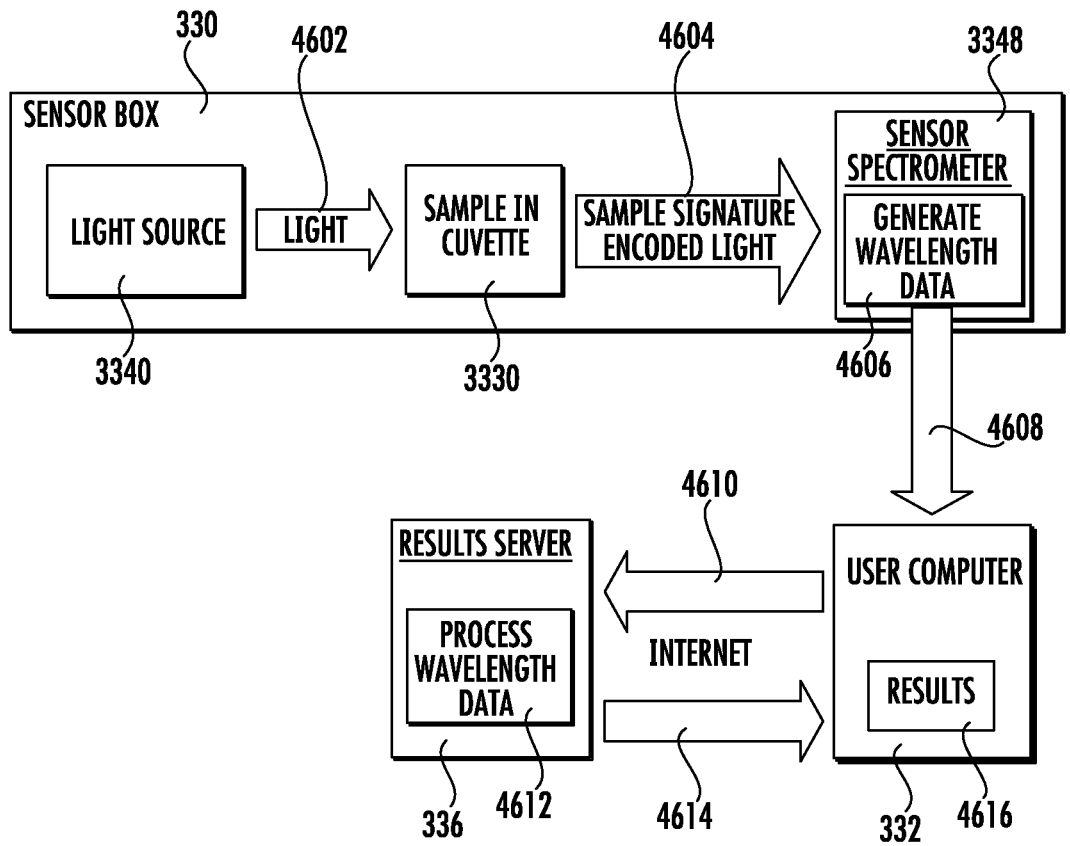
FIG. 46 shows a system and process for analyzing a sample.

FIG. 46 shows a process for spectroscopic analysis of a sample. The Sensor Box collects optical data from the beverage sample of interest. The computational components process the optical data by searching for optical resonant frequencies or wavelengths in the sample data consistent with the parameter/property of interest's molecular signature. With specific reference to FIG. 46, at step 4602, light from light source, e.g. lamp 3340, is projected through a sample in the cuvette 3300. The light source produces light in a spectrum of wavelengths sufficient to produce the wavelength signature for the particular parameter/property under investigation. Wavelengths may include, without limitation, visible light, UV, infra-red, etc. At step 4604, light altered by the sample, i.e. encoded by the sample signature, is received into the spectrometer 3348. The spectrometer 3348 processes the sample light signature into wavelength components (step 4606) which are passed to a computer 332 (step 4608). The computer 332 passes the spectrum data to a results server 336 over a suitable communications channel such as the internet (step 4610). The server 336 processes the spectrum (step 4612) by applying algorithms pertaining to the pathogen under investigation to determine if the sample spectrum indicates the presence of the pathogen under investigation. The results are passed from the server 336 to the computer 332 (step 4614) for display to the user on the user interface (step 4616). Typically, the results display will be a relatively simple indication that the sample is positive/negative to the pathogen of interest. Additional data, including quantitative data, confidence levels, etc. may also be displayed.

The processing of the sample data has two components to it, an Offline and Online.

Offline:

Multivariate Data Analysis is specifically used, or is one method example used, to determine spectral wavelengths and their associated regression coefficients needed to determine the (1) concentration range of a property of interest, and (2) to quantify or determine the concentration amount of the property if desired.

Online:

(ii) Multiple Linear Regression (MLR) methods are used successively to determine if the concentration range of a property/parameter of interest present in a test sample using wavelengths, determined offline, as independent variables (x). MLR output y is given as $$y = \beta_0 + \beta_1 x_1 + \beta_2 x_2 + \ldots + \beta_n x_n$$

Where $b_0$ is the regression constant;
$b_1$ to $b_n$ are regression coefficients; and
$x_1$ to $x_n$ are the virus resonant/discerning wavelengths.

The MLR output (y) is used as an indicator if the property of interest's concentration amount falls in a range or "class". The MLR models diagnose the sample data and if the output, y, outputs within range e.g., between 0.5 and 1.35 then the concentration is within that range. If desired a quantification method, such as Partial Least Squares (PLS) which is structured in a manner identical the classifier regression model method above, is used to output the exact concentration amount. The output concentration amount should be within the range determined by the range determining process described above.

Figure 47:
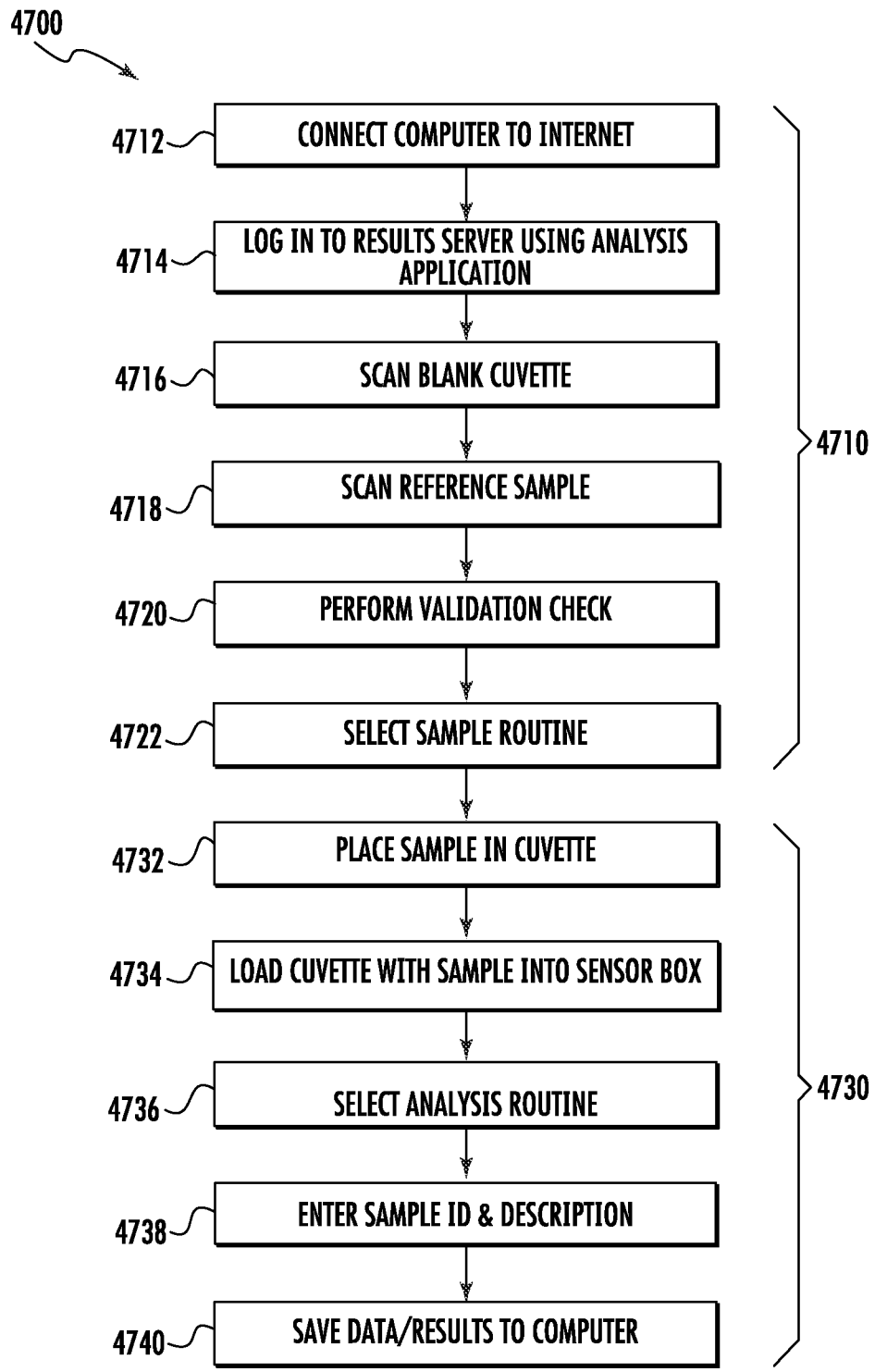
FIG. 47 shows an operational flow for a user to execute an analysis application on a computer.

FIG. 47 shows the analysis process coupled with the test apparatus. The process 4700 includes an initialization phase, and a sample test phase. The test phase can be expected to take approximately 5 minutes to produce the result being sought. At step 4710, the analyzer may be initialized. Initialization may include connecting the user computer 332 to the internet (step 4712) and logging on to the results server 336 via a specific sample application or user interface on the user computer 332 (step 4714). The analyzer may be calibrated by scanning a blank cuvette with the light off 4716, scanning a reference fluid (e.g. distilled water) in a cuvette (light on) 4718 and performing a validation check 4720. The user may then select a sample routine on a GUI of the user computer 332 (step 4722) including selecting the beverage sample test. Selection of a sample test in turn selects the wavelengths and coefficients to be used for both the MLR and PLS models. The analysis application executing on the user computer 332 may provide a series of prompts to guide the user through the initialization phase.

In the sample analysis phase 4730, a cuvette is filled with beverage sample (step 4732). The cuvette is loaded into the sensor box 330 (4734). The GUI on the user computer 332 may direct these steps. At step 4736, the user selects to scan the sample on the GUI, which causes the user computer to actuate the spectrometer within the sensor box. As soon as the user clicks on the Graphical User Interface, the process continues automatically between the sensor box, computer and results server, with the spectrometer providing spectral data to the computer, which is then forwarded to the results server, and with the computer receiving results data from the results server. At this time, the user may enter a Sample ID and description for the sample, such as details of the beverage sample, time, location of test, etc. (step 4738). The user may then store the received results against the sample ID 4740. The results are received relatively quickly, as fast as within a few seconds. They are output in plain English with no need for the user to read and interpret complex scientific codes.

An advantage of this system is that the tests require no sample preparation. Thus no highly skilled personnel are needed, and results are output after just a mouse click on the GUI of the analysis application.

The test system described is able to analyze for detect various beverage properties at a time or simultaneously.

It is advantageous that the presently described systems and methods can be used to simultaneously test for various sample properties or parameters.

Figure 48:
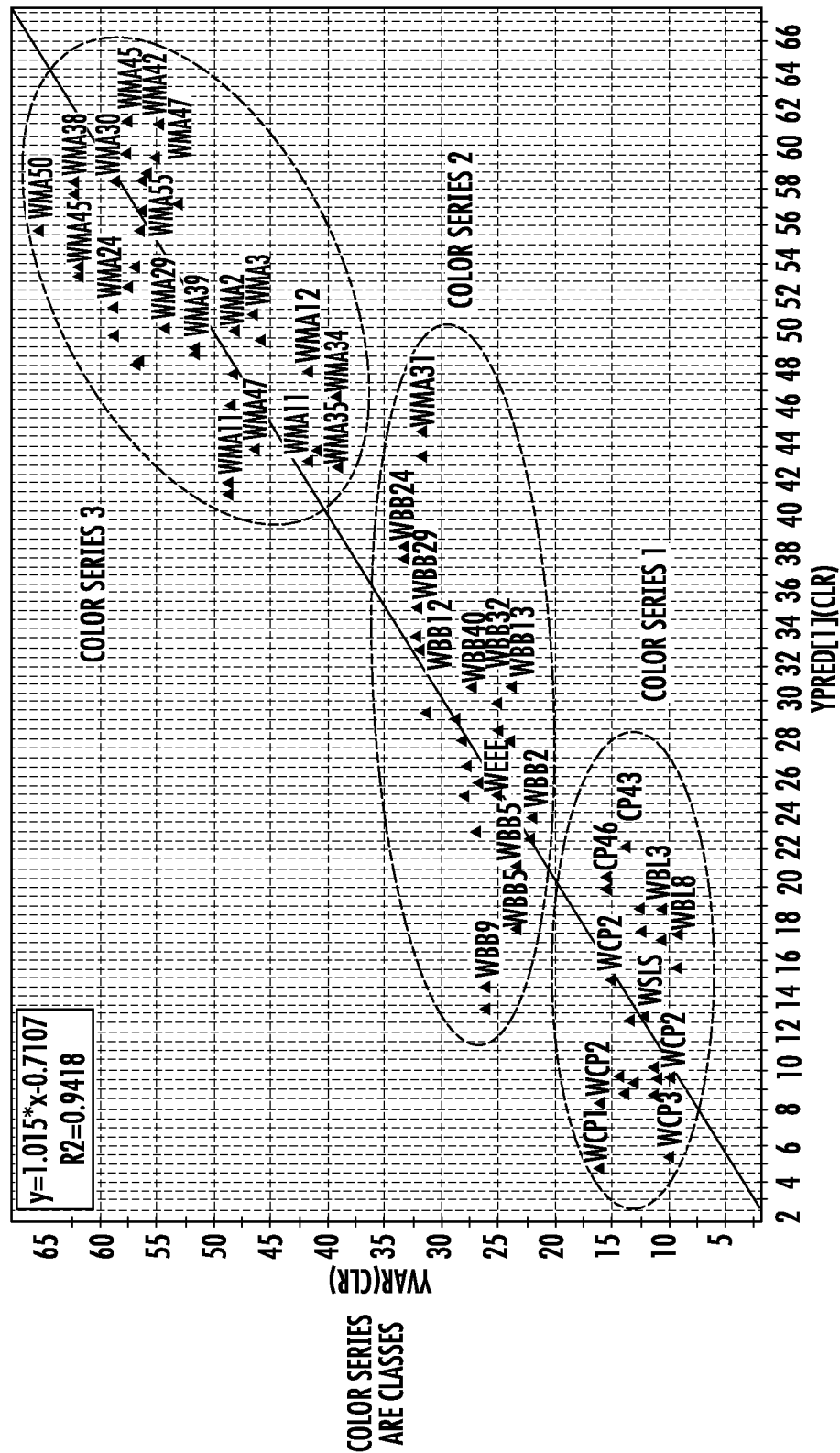
FIG. 48 shows a UCM model for color data of a beverage.
Figure 49:
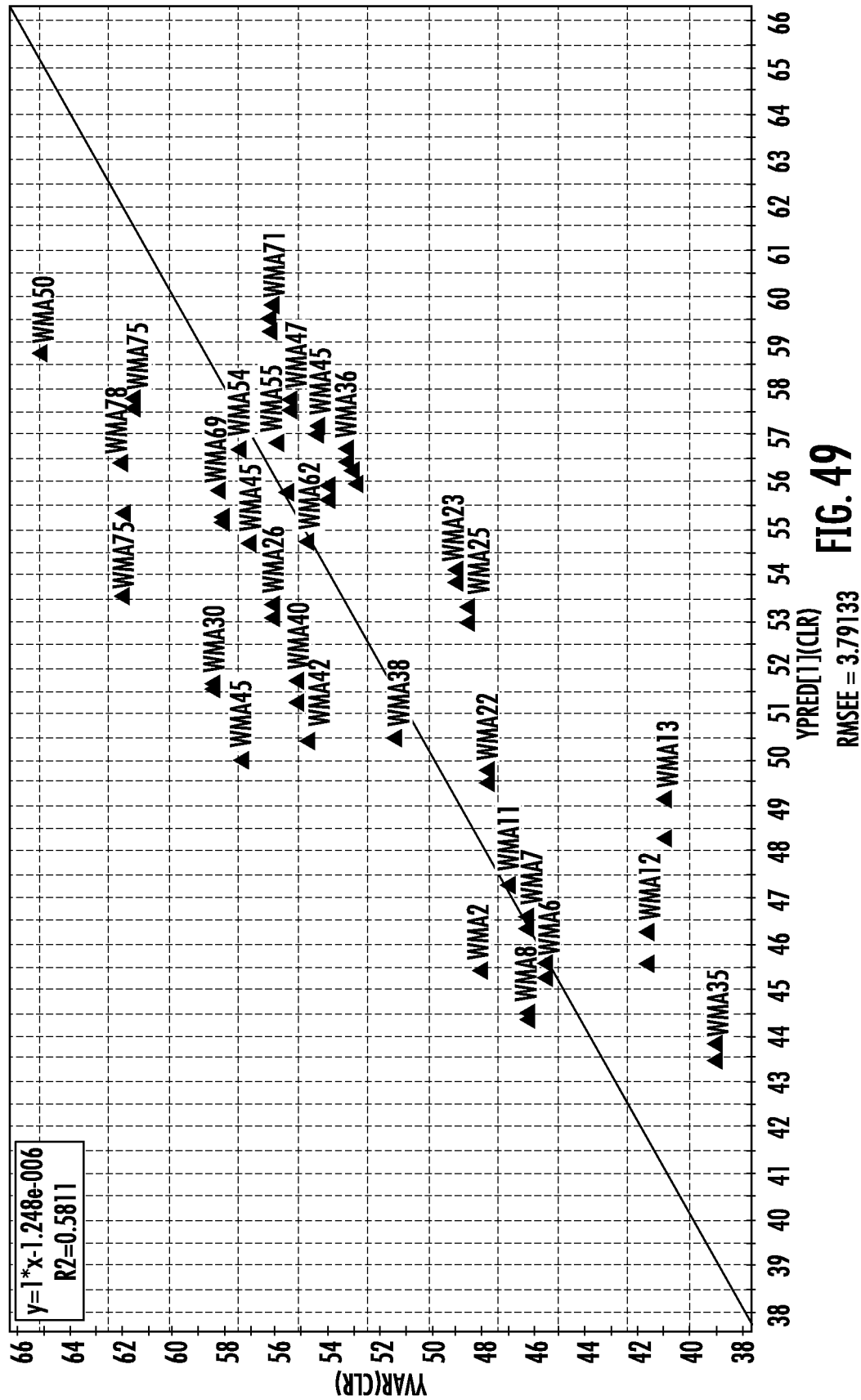
FIG. 49 shows a PMM model for color data of a beverage.
Figure 50:
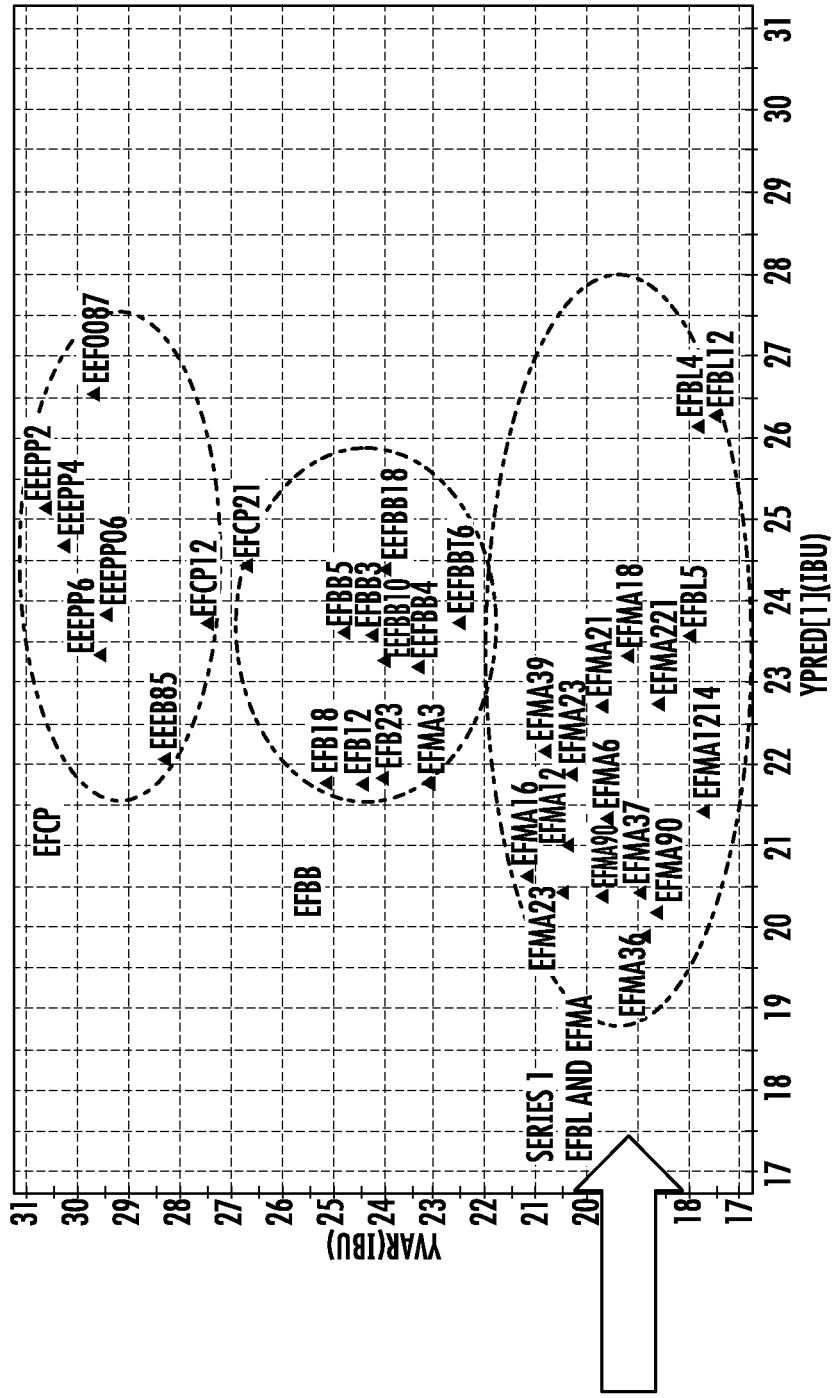
FIG. 50 shows a UCM model for bitterness data of a beverage.
Figure 51:
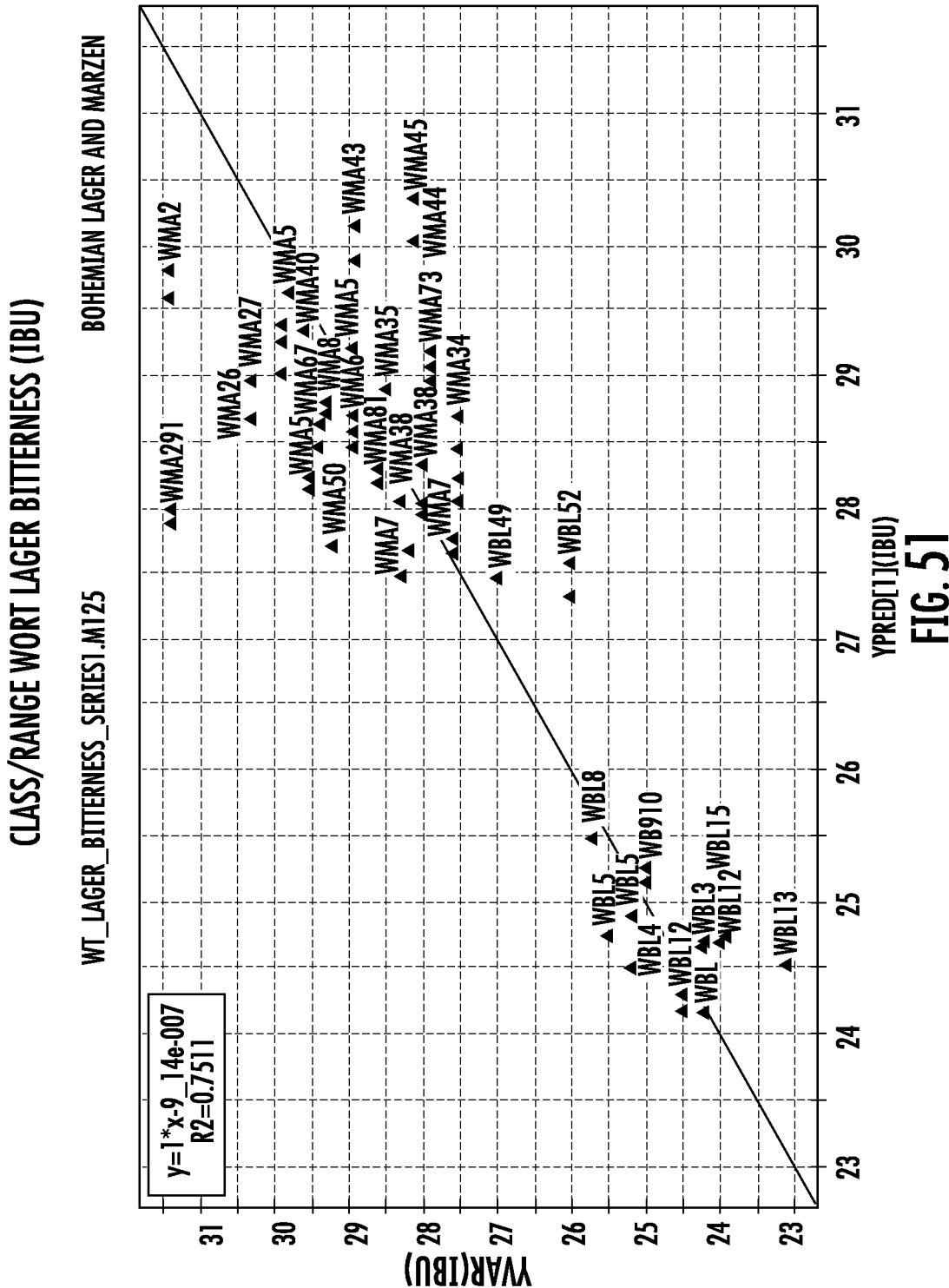
FIG. 51 shows a PMM model for bitterness data of a beverage.
Figure 52:
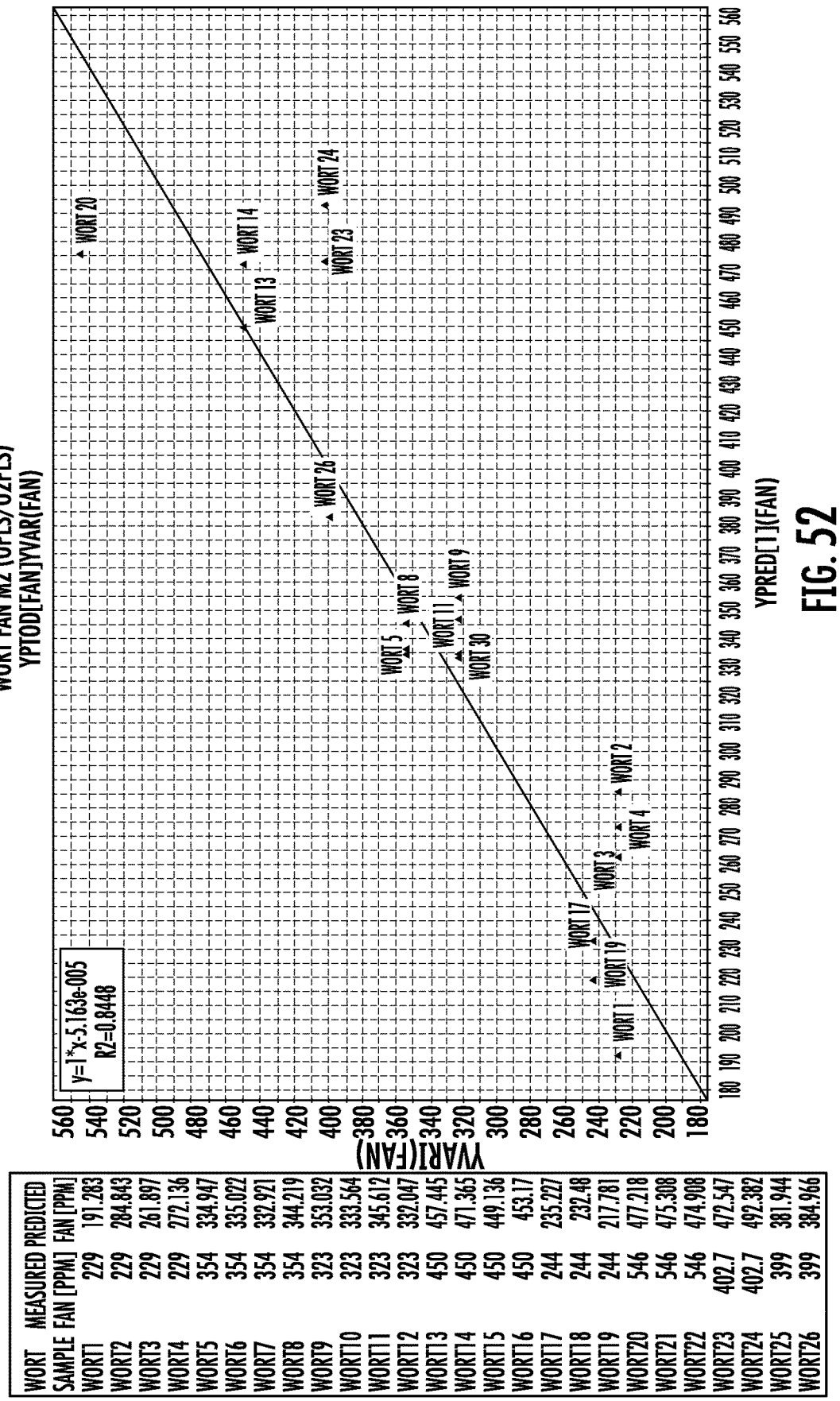
FIG. 52 shows a FAN prediction graph for a beverage.

As described herein, a variety of beverage parameters may be analyzed using the systems and methods of the described embodiments. Parameters include beverage color, bitterness, Free Amino Nitrogen (FAN), yeast count and yeast viability. FIGS. 48 and 49 show UCM and PMM plots respectively for color of a Wort Lager. FIGS. 50 and 51 show UCM and PMM plots respectively for bitterness of a beverage. FIG. 52 shows a prediction plot for FAN of a Wort Lager beverage.

Figure 53:
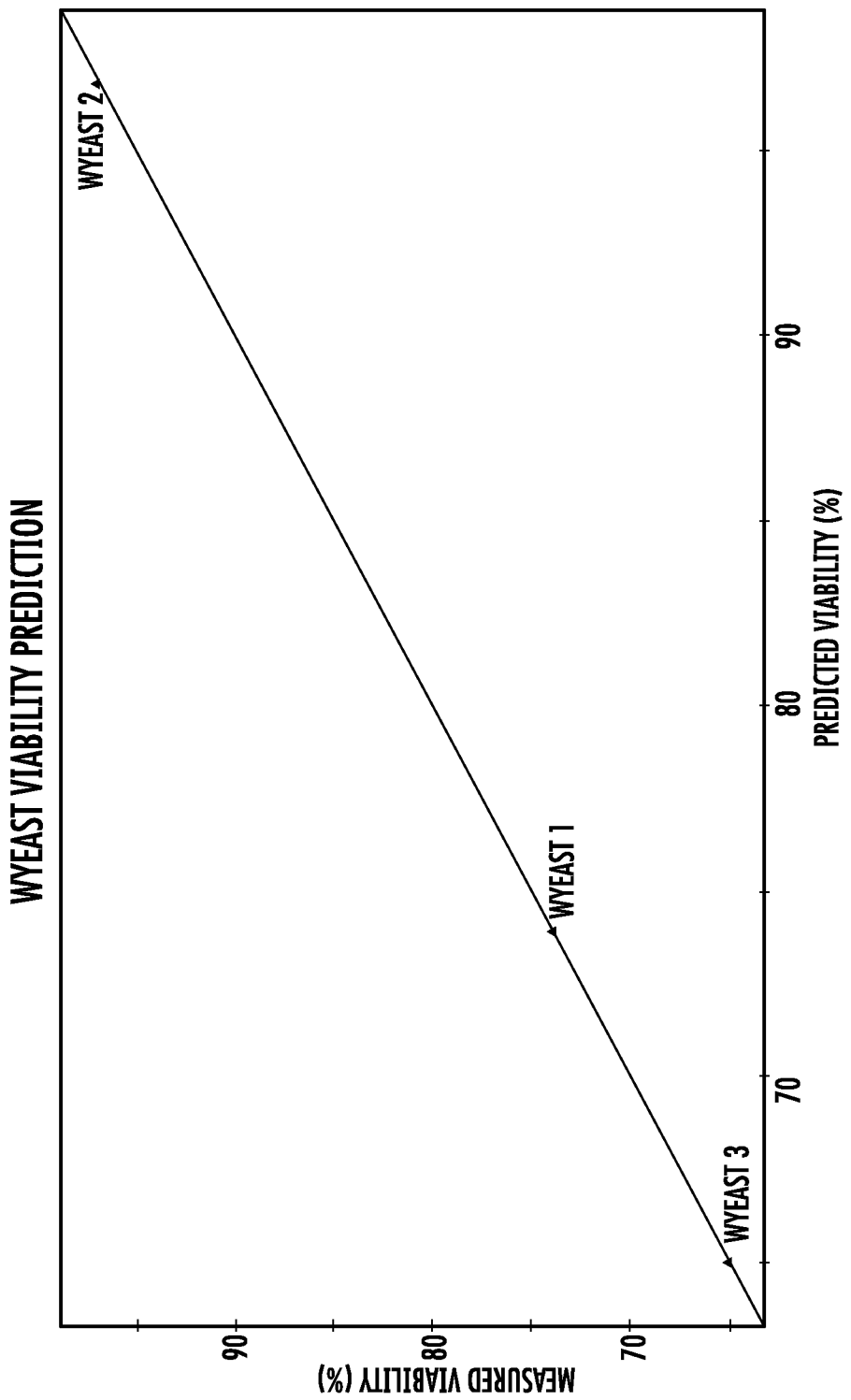
FIG. 53 shows a yeast viability prediction graph for a beverage.
Figure 55:
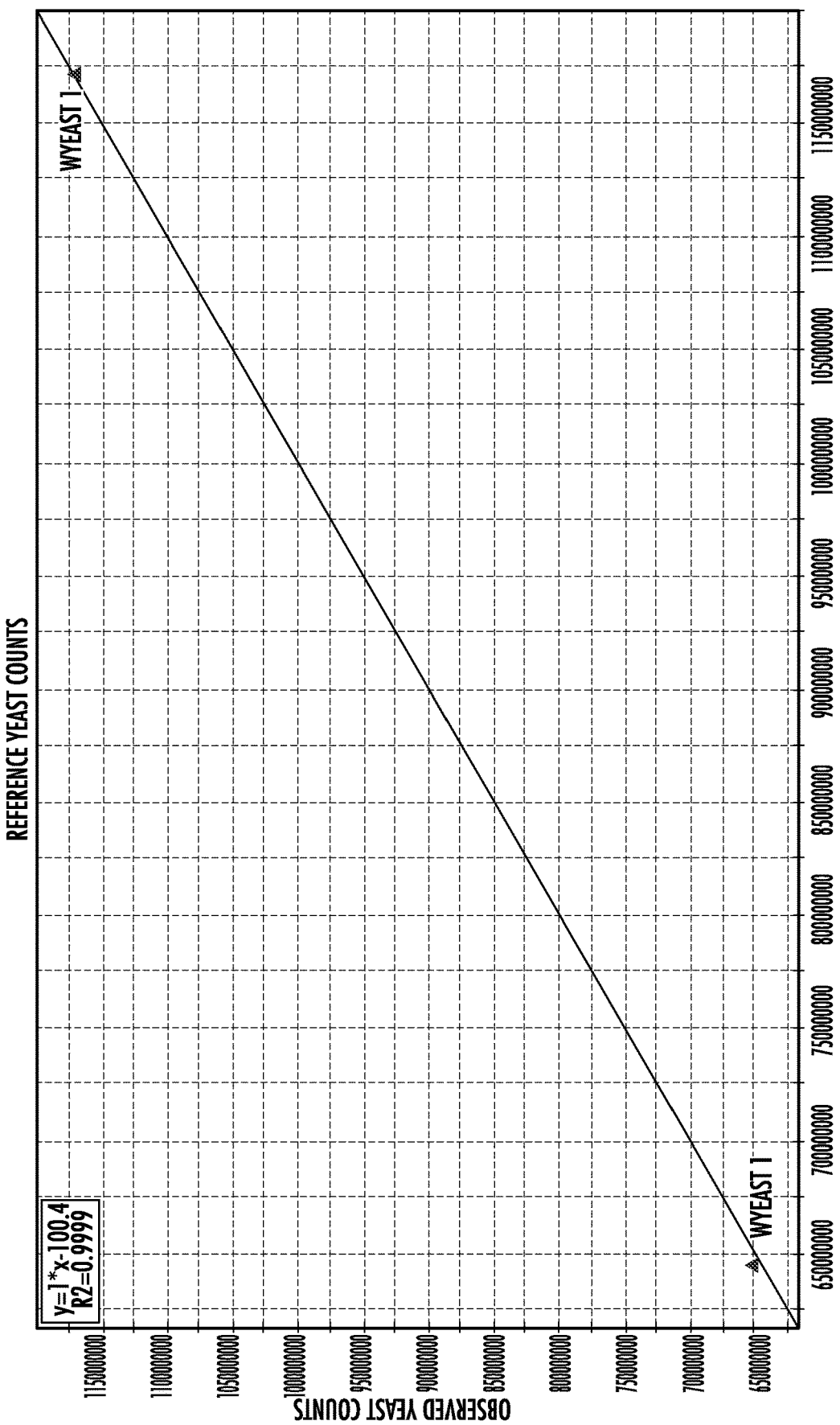
FIG. 55 shows a yeast count graph for a beverage.

Yeast viability can be predicted using UV-VIS and NIR spectrographic data. Spectral data ranging from 300 to 850 nm of yeast was acquired using the spectrometer. Samples with different dilution ratios and data formats i.e. linear and log data was acquired. FIGS. 53 to 56 shows sample data from samples obtained using a standard cuvette (10 mm×10 mm) of wyeast slurry with 200 ml of water. FIGS. 53 and 54 show yeast viability prediction, while FIGS. 55 and 56 show yeast count data. The results include the spectra and viability prediction results have average % difference of less than 3%. The model equations used to predict the viability as shown in FIGS. 53 and 54 can be packaged into a single handheld microcomputer-powered unit for rapid analyzes of yeast viability. In addition, yeast viability confounding factors such as pH, osmolality and bacteria can also be predicted by such a unit. This will give users both a means to measure, control and optimize cell culture/yeast viability.

The spectroscopic analysis systems and methods described have many advantages over more complicated testing systems. Advantages include:

REAGENTS AND CONSUMABLES: No reagents needed/no supply chain issues, just distilled water needed.

NON-DESTRUCTIVE 100% DIRECT TESTS: No interfering/sample degrading chemicals are required.

THROUGHPUT: Each sensor box can produce 100 real time results per 8-hour shift.

COST: Current lab tests tests are in the double to triple digit range while our cost per sample test for the present optical technology can be as little as $5 for a test.

PERSONNEL: Highly skilled lab technicians are required to administer current tests lab tests. By contrast, anyone can operate the sensor box analyzer including clericals, admins, etc.

FOOTPRINT: The sensor box is about the size of a shoebox and weighs approximately 3 pounds thus can easily be taken to the sample(s) or from place to place.

WORKER SAFETY: The Sensor Box and the computer can be as far part as possible, or even in different rooms/cubicles, depending on the length of the USB cable used for those allergic to alcoholic beverages.

REAL-TIME RESULTS RELEASE: The sensor box analyzer results are produced almost instantly, while most lab tests require at least hours to days to be completed.

RESULTS INTERPRETATION: Expressed plain English.

The sensor box system and computer application can be distributed to multiple sites for ready implementation of a high intensity testing regime. Locations may include labs, field, manufacturing plants, etc. People with modest income will find the analyzer tests much more affordable/accessible and further since the system is easy to operate and the costs are highly subdued compared to a traditional lab.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given.

What is claimed is:

1. A method for determining one or more beverage parameters of a beverage comprising:
   (A) obtaining a beverage sample;
   (B) obtaining spectrographic data from the beverage sample;
   (C) determining by a data processor and from the spectrographic data, a value range of the one or more beverage parameters; and
   (D) determining by the data processor and from the spectrographic data, a value of the one or more beverage parameters;
   wherein the one or more beverage parameters comprise one or more of Free Amino Nitrogen (FAN) and yeast viability.

2. The method of claim 1 wherein determining the one or more beverage parameters comprises:
   (A) selecting a beverage parameter of the one or more beverage parameters; and
   (B) performing a classification procedure on the spectrographic data that determines a class for the selected beverage parameter, the class comprising a range of beverage parameter values.

3. The method of claim 2, wherein performing the classification procedure comprises:
   (A) executing a universal calibration model that estimates a first class that the spectrographic data belongs to comprising a first range of parameter values for the selected beverage parameter; and
   (B) executing a parameter membership classifier model that determines a second class that the spectrographic data belongs to, the second class comprising a second range of parameter values for the selected beverage parameter.

4. The method of claim 3 further comprising comparing the first class and the second class.

5. The method of claim 4, wherein if the first class and the second class are equal, then determining at least one of the first class or the second class as the class for the selected beverage parameter.

6. The method of claim 4, wherein if the first class and the second class are not equal, then filtering the spectrographic data to remove data that is not between the first range and the second range, and re-executing the universal calibration model and the parameter membership classifier model on the filtered spectrographic data.

7. The method of claim 6 further comprising repeating the executing the universal calibration model, the executing the parameter membership classifier model, and the filtering the spectrographic data until the first class determined by the universal calibration model is equal to the second class determined by the parameter membership classifier model.

8. The method of claim 2 further comprising performing a quantification procedure for the selected beverage parameter that processes the determined class for the selected beverage parameter and calculates a result value within the range of beverage parameter values for the selected beverage parameter.

9. The method of claim 8, wherein performing the quantification procedure comprises:
   (A) retrieving at least one equation for the determined class from a library;
   (B) executing the at least one equation to calculate the result value.

10. The method of claim 8 further comprising performing the classification procedure and the quantification procedure for each beverage parameter.

11. The method of claim 1 further comprising selecting a beverage parameter of interest, wherein the selection determines a Multiple Linear Regression equation to be used for analyzing the beverage sample.

12. The method of claim 1 further comprising:
   (A) receiving the beverage sample into a sensor unit comprising a light source and a spectrometer;
   (B) obtaining the spectrographic data within the sensor unit;
   (C) communicating the spectrographic data from the sensor unit to a results server;
   (D) processing the spectrographic data in the results server to determine a result indicating presence/absence and/or concentration of the one or more beverage parameters in the beverage sample; and
   (E) communicating the result from the results server to a computer coupled to the sensor unit.

13. The method of claim 1 further comprising processing the spectrographic data in the data processor to assign wavelength and wavelength intensities to the spectrographic data.

14. A system for analyzing a beverage comprising:
   (A) spectroscopic apparatus configured to receive a beverage sample and dispose the beverage sample in a light beam to obtain spectrographic data of the beverage sample; and
   (B) a data processor programmed to:
      (a) receive the spectrographic data from the spectroscopic apparatus;
      (b) determine a value range of at least one beverage parameter of the beverage sample, wherein the at least one beverage parameter comprises at least one of Free Amino Nitrogen (FAN) and yeast viability;
      (c) determine a value of the at least one beverage parameter from the spectrographic data.

15. The system of claim 14, wherein the data processor is programmed to:
   (A) communicate the spectrographic data to a results server;
   (B) receive a result from the results server that indicates the at least one-beverage parameter; and
   (C) display the result.

16. The system of claim 15 wherein the data processor is programmed to:
   (A) execute a user interface that enables a user to select the at least one beverage parameter;
   (B) communicate the selection to the results server;
   (C) wherein the selection of the at least one beverage parameter determines a Multiple Linear Regression equation to be used for determining the value range of the at least one beverage parameter; and
   (D) wherein the selection of the at least one beverage parameter determines a Partial Least Squares regression equation to be used for determining the value of the at least one beverage parameter.

17. A method for determining one or more beverage parameters of a beverage comprising:
   (A) obtaining a beverage sample;
   (B) obtaining spectrographic data from the beverage sample;
   (C) performing a range determining procedure for at least one parameter of the one or more beverage parameters that determines a range of parameter values for the at least one beverage parameter wherein the one or more beverage parameters comprises one or more of color and bitterness;

(D) performing a quantification procedure on the determined range to determine one or more values for the at least one beverage parameter for the determined range;
(E) wherein the range determining procedure comprises:
  (a) executing a universal calibration model that estimates a first range of parameter values that the spectroscopic data belongs to for the at least one beverage parameter; and
  (b) executing a parameter membership classifier model that estimates a second range of parameter values that the spectroscopic data belongs to for the at least one beverage parameter;
(F) wherein the quantification procedure comprises:
  (a) retrieving at least one equation for calculating the at least one beverage parameter, wherein the at least one equation is dependent on the determined range for the at least one beverage parameter;
  (b) applying the at least one equation on the spectroscopic data to determine the one or more values for the at least one beverage parameter from the spectroscopic data.

\* \* \* \* \*